(12) United States Patent
Freeman et al.

(10) Patent No.: US 7,537,571 B2
(45) Date of Patent: May 26, 2009

(54) INTEGRATED BLOOD SAMPLING ANALYSIS SYSTEM WITH MULTI-USE SAMPLING MODULE

(75) Inventors: Dominique M. Freeman, La Honda, CA (US); Ganapati Mauze, Sunnyvale, CA (US); Dirk Boecker, Palo Alto, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 537 days.

(21) Appl. No.: 10/363,507

(22) PCT Filed: Jun. 12, 2002

(86) PCT No.: PCT/US02/19059

§ 371 (c)(1),
(2), (4) Date: Nov. 26, 2003

(87) PCT Pub. No.: WO02/101359

PCT Pub. Date: Dec. 19, 2002

(65) Prior Publication Data

US 2004/0092842 A1    May 13, 2004

(51) Int. Cl.
*A61B 5/00* (2006.01)
(52) U.S. Cl. .................................. 600/583; 606/181
(58) Field of Classification Search ............... 600/573, 600/575, 576, 577, 578, 579, 580, 581, 582, 600/583, 584; 606/181, 182, 183, 184, 185, 606/186
See application file for complete search history.

(56) References Cited

U.S. PATENT DOCUMENTS

| | | | |
|---|---|---|---|
| 2,801,633 A | 8/1957 | Mauze, et al. | |
| 3,358,689 A | 12/1967 | Higgins | 128/329 |
| 3,494,358 A | 2/1970 | Grossenbacher | 128/218 |
| 3,626,929 A | 12/1971 | Sanz | 128/2 R |
| 3,742,954 A | 7/1973 | Strickland | 128/302 |
| 3,953,172 A | 4/1976 | Shapiro | 23/230 |
| 4,224,125 A | 9/1980 | Nakamura | 204/195 B |
| 4,230,118 A | 10/1980 | Holman et al. | 128/314 |

(Continued)

FOREIGN PATENT DOCUMENTS

DE    4420232    12/1995

(Continued)

OTHER PUBLICATIONS

International Search Report (PCT/ISA/220) for PCT/US02/19058. (all references are being submitted herewith or were submitted in a previous Information Disclosure Statement).

(Continued)

*Primary Examiner*—Max Hindenburg
*Assistant Examiner*—Sharick Naqi
(74) *Attorney, Agent, or Firm*—Paul Davis; Goodwin Procter LLP

(57) ABSTRACT

A simple, miniaturized, disposable acquisition and test module for monitoring glucose or other analytes successively for multiple times is described. The apparatus is designed to collect and test small volumes of blood in a single step. Many samples can be acquired and analyzed using a single disposable sampling module, minimizing the number of disposables and improving ease of use of the system.

11 Claims, 2 Drawing Sheets

U.S. PATENT DOCUMENTS

| | | | |
|---|---|---|---|
| 4,338,174 A | 7/1982 | Tamura | 204/195 |
| 4,340,669 A | 7/1982 | Bauer | 435/14 |
| 4,353,984 A | 10/1982 | Yamada | 435/14 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,420,564 A | 12/1983 | Tsuji et al. | 435/288 |
| 4,426,451 A | 1/1984 | Columbus | 436/518 |
| 4,426,884 A | 1/1984 | Polchaninoff | 73/172 |
| 4,469,110 A | 9/1984 | Slama | 128/770 |
| 4,517,978 A | 5/1985 | Levin | 128/314 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,590,411 A | 5/1986 | Kelly | 318/687 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,637,393 A | 1/1987 | Ray | 128/305 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,758,323 A | 7/1988 | Davis | 204/403 |
| 4,794,926 A * | 1/1989 | Munsch et al. | 606/183 |
| RE32,922 E | 3/1989 | Levin | 128/314 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,824,639 A | 4/1989 | Hildenbrand | 422/56 |
| 4,827,763 A | 5/1989 | Bourland | 73/172 |
| 4,830,959 A | 5/1989 | McNeill | 435/53 |
| 4,836,904 A | 6/1989 | Armstron | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 128/634 |
| 4,897,173 A | 1/1990 | Nankai | 204/403 |
| 4,900,424 A | 2/1990 | Birch | 204/409 |
| 4,911,794 A | 3/1990 | Parce | 204/1 T |
| 4,920,977 A | 5/1990 | Haynes | 128/770 |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,999,582 A | 3/1991 | Parks | 324/438 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| 5,029,583 A | 7/1991 | Meserol | |
| 5,054,499 A | 10/1991 | Swierczek | 128/770 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,216,597 A | 6/1993 | Beckers | 364/413.02 |
| 5,217,480 A | 6/1993 | Haber | 606/182 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,673 S | 12/1993 | Cerola | D24/147 |
| 5,272,087 A | 12/1993 | El Murr | 435/291 |
| 5,277,181 A | 1/1994 | Mendelson | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollmann | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |
| 5,314,442 A | 5/1994 | Susumu | 606/182 |
| 5,316,012 A | 5/1994 | Siegal | 128/744 |
| 5,316,229 A | 5/1994 | Evans | 606/171 |
| 5,318,583 A | 6/1994 | Rabenau et al. | 606/182 |
| 5,320,607 A | 6/1994 | Ishibashi | 604/115 |

| | | | | | | |
|---|---|---|---|---|---|---|
| 5,324,302 A | 6/1994 | Crouse ....................... 606/181 | | 5,628,764 A | 5/1997 | Schraga ..................... 606/182 |
| 5,324,303 A | 6/1994 | Strong ........................ 606/181 | | 5,628,765 A | 5/1997 | Susumu ..................... 606/182 |
| 5,332,479 A | 7/1994 | Uenoyama ............. 204/153.12 | | 5,628,890 A | 5/1997 | Carter ........................ 204/403 |
| 5,350,392 A | 9/1994 | Purcell ........................ 606/182 | | 5,640,954 A | 6/1997 | Pfeiffer ...................... 128/635 |
| 5,352,351 A | 10/1994 | White ......................... 204/406 | | 5,643,306 A | 7/1997 | Schraga ..................... 606/182 |
| 5,354,287 A | 10/1994 | Wacks ........................ 604/232 | | 5,645,555 A | 7/1997 | Davis ......................... 606/182 |
| 5,354,447 A | 10/1994 | Uenoyama .................. 204/403 | | 5,650,062 A | 7/1997 | Ikeda ......................... 205/778 |
| 5,356,420 A | 10/1994 | Czernecki ................... 606/182 | | 5,653,863 A | 8/1997 | Genshaw ................. 205/777.5 |
| 5,360,410 A | 11/1994 | Wacks ........................ 604/232 | | 5,657,760 A | 8/1997 | Ying et al. ............. 128/660.03 |
| 5,366,469 A | 11/1994 | Steg ........................... 606/182 | | 5,658,444 A | 8/1997 | Black ......................... 204/415 |
| 5,366,470 A | 11/1994 | Ramel ........................ 606/183 | | 5,662,127 A | 9/1997 | De Vaughn ................. 128/765 |
| 5,366,609 A | 11/1994 | White ......................... 204/403 | | 5,662,672 A | 9/1997 | Pambianchi ................ 606/181 |
| 5,371,687 A | 12/1994 | Holmes ....................... 364/514 | | 5,676,143 A | 10/1997 | Simonsen ................... 128/633 |
| 5,375,397 A | 12/1994 | Ferrand ......................... 54/66 | | 5,680,858 A | 10/1997 | Hansen-Egesborg ........ 128/635 |
| 5,378,628 A | 1/1995 | Graetzel .................... 435/288 | | 5,680,872 A | 10/1997 | Sesekura .................... 128/760 |
| 5,382,346 A | 1/1995 | Uenoyama .................. 204/403 | | 5,682,884 A | 11/1997 | Hill ............................ 128/637 |
| 5,383,885 A | 1/1995 | Bland ......................... 606/182 | | 5,683,562 A | 11/1997 | Schaffar ..................... 204/403 |
| 5,389,534 A | 2/1995 | Gentezkow ................. 435/180 | | 5,695,947 A | 12/1997 | Guo ............................ 435/11 |
| 5,393,903 A | 2/1995 | Graetzel .................... 556/137 | | 5,700,695 A | 12/1997 | Yassinzadeh ............... 436/180 |
| 5,395,387 A | 3/1995 | Burns ......................... 606/181 | | 5,705,045 A | 1/1998 | Park ........................... 204/403 |
| 5,397,334 A | 3/1995 | Schenk ....................... 606/182 | | 5,708,247 A | 1/1998 | McAleer ..................... 204/403 |
| 5,401,376 A | 3/1995 | Foos .......................... 204/415 | | 5,709,668 A | 1/1998 | Wacks ........................ 604/232 |
| 5,402,798 A | 4/1995 | Swierczek .................. 128/770 | | 5,709,699 A | 1/1998 | Warner ....................... 606/181 |
| 5,405,511 A | 4/1995 | White ........................ 204/153.1 | | 5,710,011 A | 1/1998 | Forrow ........................ 435/25 |
| 5,407,545 A | 4/1995 | Hirose .................... 204/153.12 | | 5,720,862 A | 2/1998 | Hamamoto .................. 204/403 |
| 5,407,554 A | 4/1995 | Saurer ........................ 204/403 | | 5,720,924 A | 2/1998 | Eikmeier .................... 422/102 |
| 5,407,818 A | 4/1995 | Gentezkow ................. 435/180 | | D392,391 S | 3/1998 | Douglas ..................... D24/225 |
| 5,409,583 A | 4/1995 | Yoshioka ................ 204/153.12 | | 5,723,284 A | 3/1998 | Ye ................................ 435/4 |
| 5,410,059 A | 4/1995 | Fraser .......................... 546/10 | | 5,727,548 A | 3/1998 | Hill ............................ 128/637 |
| 5,423,847 A | 6/1995 | Strong et al. ............... 606/182 | | 5,730,753 A | 3/1998 | Susumu ...................... 606/181 |
| 5,436,161 A | 7/1995 | Bergstrom .................. 435/291 | | 5,733,300 A | 3/1998 | Pambianchi ................. 606/181 |
| 5,437,999 A | 8/1995 | Diebold ...................... 435/288 | | D393,716 S | 4/1998 | Brenneman ................. D24/147 |
| 5,438,271 A | 8/1995 | White ......................... 324/444 | | D393,717 S | 4/1998 | Brenneman ................. D24/147 |
| 5,443,701 A | 8/1995 | Willner ....................... 204/153 | | 5,741,228 A | 4/1998 | Lambrecht .................... 604/93 |
| 5,445,920 A | 8/1995 | Saito .......................... 430/311 | | 5,741,634 A | 4/1998 | Nozoe ............................ 435/4 |
| D362,719 S | 9/1995 | Kaplan ....................... D24/147 | | RE35,803 E | 5/1998 | Lange ......................... 606/182 |
| 5,454,828 A | 10/1995 | Schraga ..................... 606/182 | | 5,746,217 A | 5/1998 | Erickson ..................... 128/760 |
| 5,456,875 A | 10/1995 | Lambert .................... 264/328.1 | | 5,746,898 A | 5/1998 | Preidel ........................ 204/403 |
| 5,464,418 A | 11/1995 | Schraga ..................... 606/182 | | 5,755,733 A | 5/1998 | Susumu ...................... 606/182 |
| 5,471,102 A | 11/1995 | Becker ........................ 310/50 | | 5,759,364 A | 6/1998 | Charlton ..................... 204/403 |
| 5,476,474 A | 12/1995 | Davis ......................... 606/182 | | 5,762,770 A | 6/1998 | Pritchard .................... 204/403 |
| 5,480,387 A | 1/1996 | Gabriel ....................... 604/134 | | 5,770,369 A | 6/1998 | Meade ........................... 435/6 |
| 5,487,748 A | 1/1996 | Marshall ..................... 606/182 | | 5,772,586 A | 6/1998 | Heinonen ................... 600/300 |
| 5,496,453 A | 3/1996 | Uenoyama ............... 205/777.5 | | 5,772,677 A | 6/1998 | Mawhirt ..................... 606/181 |
| 5,498,542 A | 3/1996 | Corey ....................... 435/283.1 | | 5,773,270 A | 6/1998 | D'Orazio .................... 435/177 |
| 5,507,288 A | 4/1996 | Bocker ....................... 128/633 | | 5,776,719 A | 7/1998 | Douglas ....................... 435/28 |
| 5,508,171 A | 4/1996 | Walling .................... 205/777.5 | | 5,779,365 A | 7/1998 | Takaki ........................ 374/161 |
| 5,509,410 A | 4/1996 | Hill ........................... 128/637 | | 5,782,852 A | 7/1998 | Foggia ........................ 606/182 |
| 5,510,266 A | 4/1996 | Bonner et al. ................. 436/43 | | 5,788,652 A | 8/1998 | Rahn ........................... 600/577 |
| 5,512,159 A | 4/1996 | Yoshioka .................... 204/403 | | 5,794,219 A | 8/1998 | Brown .......................... 705/37 |
| 5,518,006 A | 5/1996 | Mawhirt ..................... 128/770 | | 5,795,725 A | 8/1998 | Buechler ..................... 435/7.1 |
| 5,524,636 A | 6/1996 | Sarvazyan .................. 128/774 | | 5,795,774 A | 8/1998 | Matsumoto ................ 435/287.9 |
| 5,525,511 A | 6/1996 | D'Costa ................... 435/287.9 | | 5,797,940 A | 8/1998 | Mawhirt ..................... 606/167 |
| 5,527,333 A | 6/1996 | Nikkels ...................... 606/182 | | 5,797,942 A | 8/1998 | Schraga ...................... 606/182 |
| 5,527,334 A | 6/1996 | Kanner ....................... 606/182 | | 5,798,030 A | 8/1998 | Raguse ....................... 204/403 |
| 5,540,709 A | 7/1996 | Ramel ........................ 606/183 | | 5,798,031 A | 8/1998 | Charlton ..................... 204/403 |
| 5,543,326 A | 8/1996 | Heller ...................... 435/287.9 | | 5,800,781 A | 9/1998 | Gavin ........................... 422/73 |
| 5,545,174 A | 8/1996 | Schenk ....................... 606/182 | | 5,801,057 A | 9/1998 | Smart ........................... 436/68 |
| 5,547,702 A | 8/1996 | Gleisner ...................... 427/2.13 | | 5,807,375 A | 9/1998 | Gross ......................... 604/890.1 |
| 5,554,166 A | 9/1996 | Lange ......................... 606/182 | | 5,820,551 A | 10/1998 | Hill ............................ 600/347 |
| 5,558,834 A | 9/1996 | Chu ............................ 422/55 | | 5,822,715 A | 10/1998 | Worthington ................. 702/19 |
| 5,569,286 A | 10/1996 | Peckham ..................... 606/181 | | 5,824,491 A | 10/1998 | Priest ........................... 435/28 |
| 5,569,287 A | 10/1996 | Tezuka ....................... 606/182 | | 5,828,943 A | 10/1998 | Brown ........................ 434/258 |
| 5,571,132 A | 11/1996 | Mawhirt ..................... 606/182 | | 5,830,219 A | 11/1998 | Bird et al. ................... 606/130 |
| 5,575,895 A | 11/1996 | Ikeda .......................... 204/403 | | 5,832,448 A | 11/1998 | Brown ........................... 705/2 |
| 5,582,697 A | 12/1996 | Ikeda .......................... 204/403 | | 5,840,020 A | 11/1998 | Heinonen ................... 600/309 |
| 5,584,846 A | 12/1996 | Mawhirt ..................... 606/181 | | 5,840,171 A | 11/1998 | Birch .......................... 205/335 |
| 5,593,852 A | 1/1997 | Heller .......................... 435/14 | | 5,849,174 A | 12/1998 | Sanghera .................... 205/775 |
| 5,609,749 A | 3/1997 | Yamauchi ................ 205/777.5 | | 5,853,373 A | 12/1998 | Griffith ....................... 600/554 |
| 5,613,978 A | 3/1997 | Harding ...................... 606/181 | | D403,975 S | 1/1999 | Douglas ...................... D10/81 |
| 5,620,279 A | 4/1997 | Genshaw et al. ............. 204/402 | | 5,857,983 A | 1/1999 | Douglas ...................... 600/538 |
| 5,624,537 A | 4/1997 | Turner et al. ................ 204/403 | | 5,860,922 A | 1/1999 | Gordon et al. .............. 600/431 |
| D379,516 S | 5/1997 | Rutter ........................ D24/146 | | 5,866,353 A | 2/1999 | Berneth ........................ 435/26 |

| Patent | Type | Date | Inventor | Class |
|---|---|---|---|---|
| 5,868,135 | A | 2/1999 | Kaufman | 128/630 |
| 5,868,772 | A | 2/1999 | LeVaughn | 606/181 |
| 5,869,972 | A | 2/1999 | Birch | 324/439 |
| 5,871,494 | A | 2/1999 | Simons et al. | |
| 5,872,713 | A | 2/1999 | Douglas | 702/85 |
| 5,873,887 | A | 2/1999 | King | 606/182 |
| 5,876,957 | A | 3/1999 | Douglas | 435/28 |
| 5,879,163 | A | 3/1999 | Brown | 434/236 |
| 5,879,310 | A | 3/1999 | Sopp | 600/578 |
| 5,879,373 | A | 3/1999 | Roeper | 606/344 |
| 5,882,494 | A | 3/1999 | van Antwerp | 204/403 |
| 5,885,211 | A | 3/1999 | Eppstein | 600/309 |
| 5,887,133 | A | 3/1999 | Brown | 395/200.3 |
| RE36,191 | E | 4/1999 | Solomon | 395/308 |
| 5,893,870 | A | 4/1999 | Talen | 606/201 |
| 5,897,493 | A | 4/1999 | Brown | 600/300 |
| 5,899,855 | A | 5/1999 | Brown | 600/301 |
| 5,900,130 | A | 5/1999 | Benvegnu | 204/453 |
| 5,906,921 | A | 5/1999 | Ikeda | 435/25 |
| D411,619 | S | 6/1999 | Duchon | D24/146 |
| 5,913,310 | A | 6/1999 | Brown | 128/897 |
| 5,916,156 | A | 6/1999 | Hildenbrand | 600/347 |
| 5,916,230 | A | 6/1999 | Brenneman | 606/172 |
| 5,918,603 | A | 7/1999 | Brown | 128/897 |
| 5,921,963 | A | 7/1999 | Erez | 604/192 |
| 5,922,188 | A | 7/1999 | Ikeda | 204/777.5 |
| 5,933,136 | A | 8/1999 | Brown | 345/327 |
| 5,935,075 | A | 8/1999 | Casscells et al. | 600/474 |
| 5,942,102 | A | 8/1999 | Hodges | 205/775 |
| 5,951,300 | A | 9/1999 | Brown | 434/236 |
| 5,951,492 | A | 9/1999 | Douglas | 600/583 |
| 5,951,493 | A | 9/1999 | Douglas et al. | 600/583 |
| 5,951,836 | A | 9/1999 | McAleer | 204/403 |
| 5,954,738 | A | 9/1999 | LeVaughn | 606/181 |
| 5,956,501 | A | 9/1999 | Brown | 395/500.32 |
| 5,958,199 | A | 9/1999 | Miyamoto | 204/403 |
| 5,960,403 | A | 9/1999 | Brown | 705/2 |
| 5,964,718 | A | 10/1999 | Duchon | 600/583 |
| 5,965,380 | A | 10/1999 | Heller | 435/14 |
| 5,971,941 | A * | 10/1999 | Simons et al. | 600/573 |
| 5,972,199 | A | 10/1999 | Heller | 205/777.5 |
| 5,972,715 | A | 10/1999 | Celentano | 436/164 |
| 5,974,124 | A | 10/1999 | Schlueter | 379/106.02 |
| 5,983,193 | A | 11/1999 | Heinonen | 705/2 |
| 5,985,116 | A | 11/1999 | Ikeda | 204/403 |
| 5,985,559 | A | 11/1999 | Brown | 435/6 |
| 5,993,400 | A | 11/1999 | Rincoe | 600/595 |
| 5,997,476 | A | 12/1999 | Brown | 600/300 |
| 5,997,561 | A | 12/1999 | Boecker | 606/182 |
| 5,997,817 | A | 12/1999 | Crismore | 422/58 |
| 5,997,818 | A | 12/1999 | Hackner | 422/67 |
| 6,001,067 | A | 12/1999 | Shults | 600/584 |
| 6,015,392 | A | 1/2000 | Douglas | 600/583 |
| 6,020,110 | A | 2/2000 | Williams | 430/315 |
| 6,022,324 | A | 2/2000 | Skinner | 600/566 |
| 6,022,366 | A | 2/2000 | Schraga | 606/181 |
| 6,023,686 | A | 2/2000 | Brown | 705/37 |
| 6,030,399 | A | 2/2000 | Ignotz | 606/167 |
| 6,030,827 | A | 2/2000 | Davis | 435/287 |
| 6,032,119 | A | 2/2000 | Brown | 705/2 |
| 6,033,421 | A | 3/2000 | Theiss | 606/186 |
| 6,033,866 | A | 3/2000 | Guo | 435/14 |
| 6,036,924 | A * | 3/2000 | Simons et al. | 422/100 |
| 6,041,253 | A | 3/2000 | Kost | 604/20 |
| 6,048,352 | A | 4/2000 | Douglas | 606/181 |
| D424,696 | S | 5/2000 | Ray | D24/169 |
| 6,056,701 | A | 5/2000 | Duchon | 600/583 |
| 6,060,327 | A | 5/2000 | Keen | 436/518 |
| 6,061,128 | A | 5/2000 | Zweig | 356/243.4 |
| 6,063,039 | A | 5/2000 | Cunningham | 600/573 |
| 6,066,103 | A | 5/2000 | Duchon | 600/583 |
| 6,066,296 | A | 5/2000 | Brady | 422/63 |
| 6,067,463 | A | 5/2000 | Jeng | 600/336 |
| 6,068,615 | A | 5/2000 | Brown | 604/207 |
| D426,638 | S | 6/2000 | Ray | D24/169 |
| 6,071,249 | A | 6/2000 | Cunningham | 600/578 |
| 6,071,250 | A | 6/2000 | Douglas | 600/583 |
| 6,071,251 | A | 6/2000 | Cunningham | 600/584 |
| 6,074,360 | A | 6/2000 | Hans-Peter | 604/57 |
| 6,077,408 | A | 6/2000 | Miyamoto | 204/403 |
| 6,080,172 | A | 6/2000 | Fujiwara | 606/166 |
| 6,083,710 | A | 7/2000 | Heller | 435/14 |
| 6,086,545 | A | 7/2000 | Roe | 600/570 |
| 6,086,562 | A | 7/2000 | Jacobsen | 604/156 |
| 6,090,078 | A | 7/2000 | Erskine | 604/198 |
| 6,093,146 | A | 7/2000 | Filangeri | 600/300 |
| 6,101,478 | A | 8/2000 | Brown | 705/2 |
| 6,103,033 | A | 8/2000 | Say | 156/73.1 |
| 6,107,083 | A | 8/2000 | Collins | 435/288 |
| 6,113,578 | A | 9/2000 | Brown | 604/207 |
| 6,120,676 | A | 9/2000 | Heller | 205/777.5 |
| 6,121,009 | A | 9/2000 | Heller | 435/14 |
| 6,122,536 | A | 9/2000 | Sun | 600/341 |
| 6,129,823 | A | 10/2000 | Hughes | 204/403.01 |
| 6,133,837 | A | 10/2000 | Riley | 340/573.1 |
| 6,134,461 | A | 10/2000 | Say | 600/345 |
| 6,144,837 | A | 11/2000 | Quy | 434/307 R |
| 6,151,586 | A | 11/2000 | Brown | 705/14 |
| 6,152,875 | A | 11/2000 | Hakamata | 600/319 |
| 6,153,069 | A | 11/2000 | Pottgen | 204/403 |
| RE36,991 | E | 12/2000 | Yamamoto | 204/403 |
| 6,155,267 | A | 12/2000 | Nelson | 128/899 |
| 6,155,992 | A | 12/2000 | Henning et al. | 600/583 |
| 6,157,442 | A | 12/2000 | Raskas | 356/39 |
| 6,161,095 | A | 12/2000 | Brown | 705/2 |
| 6,162,611 | A | 12/2000 | Heller | 435/14 |
| 6,167,362 | A | 12/2000 | Brown | 703/11 |
| 6,167,386 | A | 12/2000 | Brown | 705/37 |
| 6,168,563 | B1 | 1/2001 | Brown | 600/301 |
| 6,171,325 | B1 | 1/2001 | Mauze et al. | 606/171 |
| 6,175,752 | B1 | 1/2001 | Say | 600/345 |
| 6,177,000 | B1 | 1/2001 | Peterson | 205/777.5 |
| 6,177,931 | B1 | 1/2001 | Alexander et al. | |
| 6,186,145 | B1 | 2/2001 | Brown | 128/897 |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,194,900 | B1 | 2/2001 | Freeman | 324/321 |
| 6,197,257 | B1 | 3/2001 | Raskas | 422/82.05 |
| 6,206,841 | B1 | 3/2001 | Cunningham et al. | 600/584 |
| 6,210,272 | B1 | 4/2001 | Brown | 463/1 |
| 6,212,417 | B1 | 4/2001 | Ikeda | 204/403.14 |
| 6,214,804 | B1 | 4/2001 | Felgner | 514/44 |
| 6,221,238 | B1 | 4/2001 | Grundig | 205/777.5 |
| 6,225,078 | B1 | 5/2001 | Ikeda | 435/25 |
| 6,230,501 | B1 | 5/2001 | Bailey | 62/51.1 |
| 6,233,471 | B1 | 5/2001 | Berner | 600/345 |
| 6,233,539 | B1 | 5/2001 | Brown | 703/11 |
| 6,240,393 | B1 | 5/2001 | Brown | 705/1 |
| 6,241,862 | B1 | 6/2001 | McAleer | 204/403 |
| 6,245,060 | B1 | 6/2001 | Loomis | 606/9 |
| 6,246,992 | B1 | 6/2001 | Brown | 705/2 |
| 6,248,065 | B1 | 6/2001 | Brown | 600/300 |
| 6,251,260 | B1 | 6/2001 | Heller | 205/777.5 |
| 6,254,831 | B1 | 7/2001 | Barnard | 422/82.08 |
| 6,256,533 | B1 | 7/2001 | Vuzhakov | 604/21 |
| 6,258,229 | B1 | 7/2001 | Winarta | 204/403 |
| 6,258,254 | B1 | 7/2001 | Miyamoto | 205/777.5 |
| 6,268,161 | B1 | 7/2001 | Han | 435/14 |
| 6,270,455 | B1 | 8/2001 | Brown | 600/300 |
| 6,270,637 | B1 | 8/2001 | Crismore | 204/403 |
| 6,272,359 | B1 | 8/2001 | Kivela | 455/567 |
| 6,281,006 | B1 | 8/2001 | Heller | 435/287.9 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |

| Patent No. | Date | Inventor | Class |
|---|---|---|---|
| 6,290,683 B1 | 9/2001 | Erez | 604/273 |
| 6,294,897 B1 | 9/2001 | Champlin | 320/153 |
| 6,295,506 B1 | 9/2001 | Heinonen | 702/104 |
| 6,299,757 B1* | 10/2001 | Feldman et al. | 205/775 |
| 6,302,844 B1 | 10/2001 | Walker | 600/300 |
| 6,302,855 B1 | 10/2001 | Lav | 600/584 |
| 6,305,804 B1 | 10/2001 | Rice | 351/221 |
| 6,306,347 B1 | 10/2001 | Mason | 422/58 |
| 6,309,535 B1 | 10/2001 | Williams | 205/777.5 |
| 6,312,612 B1 | 11/2001 | Sherman | 216/2 |
| 6,322,574 B1 | 11/2001 | Lloyd | 606/181 |
| 6,329,161 B1 | 12/2001 | Heller | 435/14 |
| 6,330,426 B2 | 12/2001 | Brown | 434/307 R |
| 6,331,163 B1 | 12/2001 | Kaplan | 600/486 |
| 6,334,363 B1 | 1/2002 | Testud | 73/862 |
| 6,334,778 B1 | 1/2002 | Brown | 434/258 |
| 6,334,856 B1 | 1/2002 | Allen | 604/191 |
| 6,338,790 B1 | 1/2002 | Feldman | 205/777.5 |
| 6,349,229 B1 | 2/2002 | Watanabe | 600/345 |
| 6,350,273 B1 | 2/2002 | Minagawa | 606/186 |
| 6,350,451 B1 | 2/2002 | Horn | 424/184.1 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,368,273 B1 | 4/2002 | Brown | 600/300 |
| 6,375,469 B1 | 4/2002 | Brown | 434/236 |
| 6,379,301 B1 | 4/2002 | Worthington | 600/309 |
| 6,379,324 B1 | 4/2002 | Gartstein | 604/22 |
| 6,381,577 B1 | 4/2002 | Brown | 705/2 |
| 6,387,709 B1 | 5/2002 | Mason | 436/164 |
| 6,399,394 B1 | 6/2002 | Dahm | 436/180 |
| 6,413,410 B1 | 7/2002 | Hodges | 205/775 |
| 6,413,411 B1 | 7/2002 | Pottgen | 205/777.5 |
| 6,421,633 B1 | 7/2002 | Heinonen | 703/11 |
| 6,428,664 B1 | 8/2002 | Bhullar | 204/403.03 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,451,040 B1 | 9/2002 | Purcell | 606/181 |
| 6,458,258 B2 | 10/2002 | Taniike | 204/403 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,475,436 B1 | 11/2002 | Schabbach | 422/64 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,745,750 B2 | 11/2002 | Hans | 435/14 |
| 6,494,830 B1 | 12/2002 | Wessel | 600/300 |
| 6,501,404 B2 | 12/2002 | Walker | 341/143 |
| 6,503,231 B1 | 1/2003 | Praunsnitz | 604/272 |
| 6,503,381 B1 | 1/2003 | Gotoh | 204/403.14 |
| 6,506,168 B1 | 1/2003 | Fathallah | 600/578 |
| 6,508,795 B1 | 1/2003 | Eppstein | 604/113 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | 600/583 |
| 6,530,937 B1 | 3/2003 | Schraga | 606/182 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2* | 4/2003 | Aceti et al. | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller et al. | 422/58 |
| 6,553,244 B2 | 4/2003 | Lesho | 600/347 |
| 6,554,381 B2 | 4/2003 | Locher | 347/7 |
| 6,555,061 B1 | 4/2003 | Leong et al. | 422/58 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Kazuo | 205/777.5 |
| 6,576,416 B2 | 6/2003 | Haviland | 435/4 |
| 6,582,573 B2 | 6/2003 | Douglas | 204/403.1 |
| 6,587,705 B1 | 7/2003 | Kim | 600/347 |
| 6,589,260 B1 | 7/2003 | Schmelzeisen-R | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,595,919 B2 | 7/2003 | Berner | 600/365 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,494 B1 | 8/2003 | Fowler | 600/570 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beaty | 205/792 |
| 6,650,915 B2 | 11/2003 | Routt | 600/319 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-R | 600/583 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Yamamoto | 204/403.14 |
| 6,743,211 B1 | 6/2004 | Prausnitz | 604/239 |

| Patent | Date | Name | Class |
|---|---|---|---|
| 6,743,635 B2 | 6/2004 | Neel | 436/95 |
| 6,749,618 B2 | 6/2004 | Levaughn | 606/182 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 5,059,789 A1 | 1/2005 | Goldman | 435/4 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,847,451 B2 | 1/2005 | Pugh | 356/436 |
| 6,489,052 B1 | 2/2005 | Uchigaki | 600/584 |
| 6,849,168 B2 | 2/2005 | Crumly | 204/416 |
| 6,849,216 B2 | 2/2005 | Rappin | 264/134 |
| 6,850,790 B2 | 2/2005 | Berner | 600/347 |
| 6,869,418 B2 | 3/2005 | Marano-Ford | 604/192 |
| 6,872,200 B2 | 3/2005 | Mann | 604/890.1 |
| 6,875,208 B2 | 4/2005 | Santini | 604/890.1 |
| 6,875,223 B2 | 4/2005 | Argauer | 606/181 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,239 B2 | 5/2005 | Elstrom | 606/41 |
| 6,887,253 B2 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,916,410 B2 | 7/2005 | Katsuki | 204/403 |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |

| Patent No. | Kind | Date | Name | Class |
|---|---|---|---|---|
| 6,949,221 | B2 | 9/2005 | Kiser | 422/56 |
| 6,951,631 | B1 | 10/2005 | Catt | 422/56 |
| 6,951,728 | B2 | 10/2005 | Qian | 435/14 |
| 6,952,603 | B2 | 10/2005 | Gerber | 600/310 |
| 6,952,604 | B2 | 10/2005 | DeNuzzio | 600/345 |
| 6,953,693 | B2 | 10/2005 | Neel | 436/149 |
| 6,954,662 | B2 | 10/2005 | Freger | 600/316 |
| 6,958,072 | B2 | 10/2005 | Schraga | 606/182 |
| 6,958,129 | B2 | 10/2005 | Galen | 422/57 |
| 6,958,809 | B2 | 10/2005 | Sterling | 356/39 |
| 6,959,211 | B2 | 10/2005 | Rule | 600/310 |
| 6,959,247 | B2 | 10/2005 | Neel | 702/19 |
| 6,960,287 | B2 | 11/2005 | Charlton | 205/775 |
| 6,960,289 | B2 | 11/2005 | Hodges | 205/778 |
| 6,964,871 | B2 | 11/2005 | Bell | 436/95 |
| 6,965,791 | B1 | 11/2005 | Hitchcock | 600/345 |
| 6,966,880 | B2 | 11/2005 | Boecker | 600/583 |
| 6,966,977 | B2 | 11/2005 | Hasegawa | 204/403.07 |
| 6,967,105 | B2 | 11/2005 | Nomura | 436/169 |
| 6,968,375 | B1 | 11/2005 | Brown | 709/224 |
| 6,969,359 | B2 | 11/2005 | Duchon | 600/583 |
| 6,969,450 | B2 | 11/2005 | Taniike | 204/403.01 |
| 6,969,451 | B2 | 11/2005 | Shin | 204/412 |
| 6,973,706 | B2 | 12/2005 | Say | 29/595 |
| 6,975,893 | B2 | 12/2005 | Say | 600/347 |
| 6,977,032 | B2 | 12/2005 | Hasegawa | 204/403.05 |
| 6,979,544 | B2 | 12/2005 | Keen | 435/6 |
| 6,979,571 | B2 | 12/2005 | Modzelewski | 436/164 |
| 6,982,027 | B2 | 1/2006 | Yagi | 204/403.06 |
| 6,983,176 | B2 | 1/2006 | Gardner | 600/310 |
| 6,983,177 | B2 | 1/2006 | Rule | 600/310 |
| 6,984,307 | B2 | 1/2006 | Zweig | 205/777.5 |
| 6,986,777 | B2 | 1/2006 | Kim | 606/182 |
| 6,986,869 | B2 | 1/2006 | Tuohy | 422/56 |
| 6,988,996 | B2 | 1/2006 | Roe | 600/584 |
| 6,989,243 | B2 | 1/2006 | Yani | 435/14 |
| 6,989,891 | B2 | 1/2006 | Braig | 356/39 |
| 6,990,365 | B1 | 1/2006 | Parker | 600/328 |
| 6,990,366 | B2 | 1/2006 | Say | 600/345 |
| 6,990,367 | B2 | 1/2006 | Kiser | 600/345 |
| 6,990,849 | B2 | 1/2006 | Bohm | 73/53.01 |
| 6,991,918 | B2 | 1/2006 | Keith | 435/31 |
| 6,991,940 | B2 | 1/2006 | Carroll | 436/514 |
| 6,994,825 | B2 | 2/2006 | Haviland | 422/58 |
| 6,997,317 | B2 | 2/2006 | Catelli | 206/438 |
| 6,997,343 | B2 | 2/2006 | May | 221/232 |
| 6,997,344 | B2 | 2/2006 | Brown | 221/258 |
| 6,997,936 | B2 | 2/2006 | Marshall | 606/181 |
| 6,998,247 | B2 | 2/2006 | Monfre | 435/14 |
| 6,998,248 | B2 | 2/2006 | Yani | 435/14 |
| 6,999,810 | B2 | 2/2006 | Berner | 600/345 |
| 7,001,343 | B2 | 2/2006 | Erickson | 600/573 |
| 7,001,344 | B2 | 2/2006 | Freeman | 600/583 |
| 7,003,337 | B2 | 2/2006 | Harjunmaa | 600/316 |
| 7,003,340 | B2 | 2/2006 | Say | 600/345 |
| 7,003,341 | B2 | 2/2006 | Say | 600/345 |
| 7,004,928 | B2 | 2/2006 | Aceti | 604/191 |
| 7,005,048 | B1 | 2/2006 | Watanabe | 204/403.04 |
| 7,005,273 | B2 | 2/2006 | Heller | 435/25 |
| 7,005,459 | B2 | 2/2006 | Hekal | 523/102 |
| 7,005,857 | B2 | 2/2006 | Stiene | 324/449 |
| 7,006,857 | B2 | 2/2006 | Braig | 600/310 |
| 7,006,858 | B2 | 2/2006 | Silver | 600/345 |
| 7,008,384 | B2 | 2/2006 | Tapper | 600/573 |
| 7,010,432 | B2 | 3/2006 | Kermani | 702/19 |
| 7,011,630 | B2 | 3/2006 | Desai | 600/309 |
| 7,011,954 | B2 | 3/2006 | Ouyang | 435/7.9 |
| 7,014,615 | B2 | 3/2006 | Erickson | 600/573 |
| 7,015,262 | B2 | 3/2006 | Leong | 523/205 |
| 7,016,713 | B2 | 3/2006 | Gardner | 600/310 |
| 7,018,568 | B2 | 3/2006 | Tierney | 252/511 |
| 7,018,848 | B2 | 3/2006 | Douglas | 436/524 |
| 7,022,217 | B2 | 4/2006 | Hodges | 205/777.5 |
| 7,022,218 | B2 | 4/2006 | Taniike | 205/777.5 |
| 7,022,286 | B2 | 4/2006 | Lemke | 422/67 |
| 7,024,236 | B2 | 4/2006 | Ford | 600/345 |
| 7,024,248 | B2 | 4/2006 | Penner | 607/60 |
| 7,024,399 | B2 | 4/2006 | Sumner | 706/45 |
| 7,025,425 | B2 | 4/2006 | Kovatchev | 300/365 |
| 7,025,774 | B2 | 4/2006 | Freeman | 606/181 |
| 7,027,848 | B2 | 4/2006 | Robinson | 600/310 |
| 7,029,444 | B2 | 4/2006 | Shin | 600/365 |
| 7,033,322 | B2 | 4/2006 | Silver | 600/486 |
| 7,033,371 | B2 | 4/2006 | Alden | 606/181 |
| 7,039,560 | B2 | 5/2006 | Kawatahara | 702/187 |
| 7,041,057 | B1 | 5/2006 | Faupel | 600/365 |
| 7,041,063 | B2 | 5/2006 | Abreu | 600/549 |
| 7,041,068 | B2 | 5/2006 | Freeman | 600/583 |
| 7,041,254 | B2 | 5/2006 | Haviland | 422/58 |
| 7,041,468 | B2 | 5/2006 | Drucker | 435/14 |
| 7,043,287 | B1 | 5/2006 | Khalil | 600/310 |
| 7,044,911 | B2 | 5/2006 | Drinan | 600/300 |
| 7,045,054 | B1 | 5/2006 | Buck | 205/778 |
| 7,045,097 | B2 | 5/2006 | Kovacs | 422/82.08 |
| 7,045,310 | B2 | 5/2006 | Buck | 435/7.93 |
| 7,045,361 | B2 | 5/2006 | Heiss | 436/172 |
| 7,047,070 | B2 | 5/2006 | Wilkinson | 604/20 |
| 7,047,795 | B2 | 5/2006 | Sato | 73/64.56 |
| 7,049,130 | B2 | 5/2006 | Carroll | 435/287.2 |
| 7,050,843 | B2 | 5/2006 | Shartle | 600/345 |
| 7,051,495 | B2 | 5/2006 | Lang | 53/475 |
| 7,052,268 | B2 | 5/2006 | Powell | 425/542 |
| 7,052,591 | B2 | 5/2006 | Gao | 204/490 |
| 7,052,652 | B2 | 5/2006 | Zanzucchi | 422/82.05 |
| 7,052,864 | B2 | 5/2006 | Durkop | 435/25 |
| 7,054,682 | B2 | 5/2006 | Young | 604/20 |
| 7,054,759 | B2 | 5/2006 | Fukunaga | 702/23 |
| D523,555 | S | 6/2006 | Loerwald | D24/146 |
| 7,056,425 | B2 | 6/2006 | Hasegawa | 204/403.04 |
| 7,056,495 | B2 | 6/2006 | Roser | 424/45 |
| 7,058,437 | B2 | 6/2006 | Buse | 600/347 |
| 7,060,059 | B2 | 6/2006 | Keith | 604/504 |
| 7,060,192 | B2 | 6/2006 | Yuzhakov | 216/11 |
| 7,061,593 | B2 | 6/2006 | Braig | 356/39 |
| 7,063,234 | B2 | 6/2006 | Giraud | 221/271 |
| 7,063,774 | B2 | 6/2006 | Bhullar | 204/403.02 |
| 7,063,775 | B2 | 6/2006 | Yamaoka | 204/403.06 |
| 7,063,776 | B2 | 6/2006 | Huang | 204/403.14 |
| 7,066,884 | B2 | 6/2006 | Custer | 600/309 |
| 7,066,885 | B2 | 6/2006 | Erickson | 600/309 |
| 7,070,564 | B2 | 7/2006 | Matzinger | 600/300 |
| 7,070,680 | B2 | 7/2006 | Bae | 204/403.04 |
| 7,073,246 | B2 | 7/2006 | Bhullar | 29/595 |
| 7,074,307 | B2 | 7/2006 | Simpson | 204/403.04 |
| 7,074,308 | B2 | 7/2006 | Mao | 204/403.14 |
| 7,077,328 | B2 | 7/2006 | Krishnaswamy | 235/472.01 |
| 7,077,828 | B2 | 7/2006 | Kuhr | 604/207 |
| 7,078,480 | B2 | 7/2006 | Nagel | 530/322 |
| 7,081,188 | B1 | 7/2006 | Cho | 204/403.04 |
| 7,083,712 | B2 | 8/2006 | Morita | 205/775 |
| 7,086,277 | B2 | 8/2006 | Tess | 73/53.01 |
| 7,087,149 | B1 | 8/2006 | Muguruma | 205/778 |
| 7,090,764 | B2 | 8/2006 | Iyengar | 205/775 |
| 7,096,053 | B2 | 8/2006 | Loeb | 600/317 |
| 7,096,124 | B2 | 8/2006 | Sterling | 702/23 |
| 7,097,631 | B2 | 8/2006 | Trautman | 604/46 |
| 7,098,038 | B2 | 8/2006 | Fukuoka | 436/164 |
| 7,103,578 | B2 | 9/2006 | Beck | 705/75 |
| 7,105,066 | B2 | 9/2006 | Schraga | 600/182 |
| 7,107,253 | B1 | 9/2006 | Sumner | 706/45 |
| 7,108,680 | B2 | 9/2006 | Rohr | 604/151 |
| 7,108,778 | B2 | 9/2006 | Simpson | 205/778 |
| 7,109,271 | B2 | 9/2006 | Liu | 525/283 |
| 7,110,112 | B2 | 9/2006 | Uchida | 356/364 |
| 7,110,803 | B2 | 9/2006 | Shults | 600/347 |
| 7,112,265 | B1 | 9/2006 | McAleer | 204/403.09 |

| Patent/Pub No. | Date | Name | Class |
|---|---|---|---|
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodoczyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0027328 A1 | 10/2001 | Lum | 606/186 |
| 2001/0045355 A1* | 11/2001 | Gephart et al. | 204/400 |
| 2001/0054319 A1 | 12/2001 | Heller | 73/849 |
| 2002/0016606 A1 | 2/2002 | Moerman | 606/181 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0120216 A1 | 8/2002 | Fritz | 600/583 |
| 2002/0120261 A1 | 8/2002 | Morris | 606/41 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 600/576 |
| 2003/0069753 A1 | 4/2003 | Brown | 705/2 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman et al. | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0111357 A1 | 6/2003 | Black | 205/775 |
| 2003/0113827 A1 | 6/2003 | Burkoth | 435/14 |
| 2003/0116447 A1 | 6/2003 | Surridge | 205/777.5 |
| 2003/0135333 A1 | 7/2003 | Aceti | 702/31 |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |

| | | | | | | | |
|---|---|---|---|---|---|---|---|
| 2003/0208140 A1 | 11/2003 | Pugh | 600/584 | 2004/0127928 A1 | 7/2004 | Whitson | 606/181 |
| 2003/0212344 A1 | 11/2003 | Yuzhakov | 600/583 | 2004/0127929 A1 | 7/2004 | Roe | 606/181 |
| 2003/0212345 A1 | 11/2003 | McAllister | 600/584 | 2004/0132167 A1 | 7/2004 | Rule | 435/287.1 |
| 2003/0212346 A1 | 11/2003 | McAllister | 600/584 | 2004/0133125 A1 | 7/2004 | Miyashita | 600/573 |
| 2003/0212347 A1 | 11/2003 | Sohrab | 600/584 | 2004/0133127 A1 | 7/2004 | Roe | 600/583 |
| 2003/0212423 A1 | 11/2003 | Pugh | 606/181 | 2004/0137640 A1 | 7/2004 | Hirao | 436/514 |
| 2003/0212424 A1 | 11/2003 | Briggs | 606/181 | 2004/0138541 A1 | 7/2004 | Ward | 600/345 |
| 2003/0212579 A1 | 11/2003 | Brown | 705/2 | 2004/0138588 A1 | 7/2004 | Saikley | 600/583 |
| 2003/0216767 A1 | 11/2003 | List | 606/181 | 2004/0138688 A1 | 7/2004 | Giraud | 606/181 |
| 2003/0217918 A1 | 11/2003 | Davies | 204/403.14 | 2004/0146958 A1 | 7/2004 | Bae | 435/14 |
| 2003/0220552 A1 | 11/2003 | Reghabi | 600/365 | 2004/0151737 A1 | 8/2004 | Yang | 435/5 |
| 2003/0220663 A1 | 11/2003 | Fletcher | 606/182 | 2004/0154932 A1 | 8/2004 | Deng | 205/777.5 |
| 2003/0223906 A1 | 12/2003 | McAllister | 422/58 | 2004/0157017 A1 | 8/2004 | Mauze | 428/35.7 |
| 2003/0225317 A1 | 12/2003 | Schell | 600/300 | 2004/0157149 A1 | 8/2004 | Hofmann | 430/131 |
| 2003/0225429 A1 | 12/2003 | Garthe | 606/182 | 2004/0157319 A1 | 8/2004 | Keen | 435/287.2 |
| 2003/0225430 A1 | 12/2003 | Schraga | 606/182 | 2004/0157338 A1 | 8/2004 | Burke | 436/147 |
| 2003/0228637 A1 | 12/2003 | Wang | 435/7.9 | 2004/0157339 A1 | 8/2004 | Burke | 436/149 |
| 2003/0229514 A2 | 12/2003 | Brown | 705/2 | 2004/0158137 A1 | 8/2004 | Eppstein | 600/347 |
| 2003/0232370 A1 | 12/2003 | Trifiro | 435/6 | 2004/0158271 A1 | 8/2004 | Hamamoto | 606/181 |
| 2003/0233055 A1 | 12/2003 | Erickson | 600/573 | 2004/0162473 A1 | 8/2004 | Sohrab | 600/345 |
| 2003/0233112 A1 | 12/2003 | Alden et al. | 606/181 | 2004/0162474 A1 | 8/2004 | Kiser | 600/345 |
| 2003/0233113 A1 | 12/2003 | Alden et al. | 606/182 | 2004/0162506 A1 | 8/2004 | Duchon | 600/583 |
| 2004/0006285 A1 | 1/2004 | Douglas | 600/583 | 2004/0162573 A1 | 8/2004 | Keheiri | 606/182 |
| 2004/0007585 A1 | 1/2004 | Griffith | 221/232 | 2004/0167383 A1 | 8/2004 | Kim | 600/365 |
| 2004/0009100 A1 | 1/2004 | Simons | 422/102 | 2004/0171057 A1 | 9/2004 | Yang | 435/6 |
| 2004/0010279 A1 | 1/2004 | Freeman | 606/182 | 2004/0171968 A1 | 9/2004 | Katsuki | 600/583 |
| 2004/0015064 A1 | 1/2004 | Parsons | 600/347 | 2004/0172000 A1 | 9/2004 | Roe | 604/361 |
| 2004/0019250 A1 | 1/2004 | Catelli | 600/1 | 2004/0173472 A1 | 9/2004 | Jung | 205/777.5 |
| 2004/0019259 A1 | 1/2004 | Brown | 600/300 | 2004/0173488 A1 | 9/2004 | Griffin | 206/363 |
| 2004/0026243 A1 | 2/2004 | Davies | 204/403.14 | 2004/0176705 A1 | 9/2004 | Stevens | 600/584 |
| 2004/0030353 A1 | 2/2004 | Schmelzeisen | 606/201 | 2004/0176732 A1 | 9/2004 | Frazier | 604/345 |
| 2004/0031682 A1 | 2/2004 | Wilsey | 204/403.1 | 2004/0178066 A1 | 9/2004 | Miyazaki | 204/403.01 |
| 2004/0034318 A1 | 2/2004 | Fritz | 604/19 | 2004/0178067 A1 | 9/2004 | Miyazaki | 204/403.1 |
| 2004/0038045 A1 | 2/2004 | Smart | 428/446 | 2004/0178216 A1 | 9/2004 | Brickwood | 221/268 |
| 2004/0039303 A1 | 2/2004 | Wurster | 600/584 | 2004/0180379 A1 | 9/2004 | van Duyne | 435/7.1 |
| 2004/0039342 A1 | 2/2004 | Eppstein | 604/200 | 2004/0182703 A1 | 9/2004 | Bell | 204/403.11 |
| 2004/0039407 A1 | 2/2004 | Schraga | 606/181 | 2004/0185568 A1 | 9/2004 | Matsumoto | 436/8 |
| 2004/0039408 A1 | 2/2004 | Abulhaj | 606/181 | 2004/0186359 A1 | 9/2004 | Beaudoin | 600/310 |
| 2004/0049219 A1 | 3/2004 | Briggs | 606/181 | 2004/0186394 A1 | 9/2004 | Roe | 600/598 |
| 2004/0049220 A1 | 3/2004 | Boecker | 606/181 | 2004/0186500 A1 | 9/2004 | Koilke | 606/181 |
| 2004/0050694 A1 | 3/2004 | Yang | 204/403.02 | 2004/0193201 A1 | 9/2004 | Kim | 606/181 |
| 2004/0054267 A1 | 3/2004 | Feldman | 600/316 | 2004/0193377 A1 | 9/2004 | Brown | 702/19 |
| 2004/0054898 A1 | 3/2004 | Heller | 205/777.5 | 2004/0194302 A1 | 10/2004 | Bhullar | 29/847 |
| 2004/0059256 A1 | 3/2004 | Perez | 422/68.1 | 2004/0197231 A1 | 10/2004 | Katsuki | 422/68.1 |
| 2004/0060818 A1 | 4/2004 | Feldman | 204/403.01 | 2004/0197821 A1 | 10/2004 | Bauer | 437/7.1 |
| 2004/0061841 A1 | 4/2004 | Black | 355/30 | 2004/0199062 A1 | 10/2004 | Petersson | 600/316 |
| 2004/0064068 A1 | 4/2004 | DeNuzzio | 600/583 | 2004/0199409 A1 | 10/2004 | Brown | 705/3 |
| 2004/0087990 A1 | 5/2004 | Boecker | 606/181 | 2004/0200720 A1 | 10/2004 | Musho | 204/403.01 |
| 2004/0092842 A1 | 5/2004 | Boecker | 600/575 | 2004/0200721 A1 | 10/2004 | Bhullar | 204/403.01 |
| 2004/0092994 A1 | 5/2004 | Briggs | 606/181 | 2004/0202576 A1 | 10/2004 | Aceti | 422/82.05 |
| 2004/0092995 A1 | 5/2004 | Boecker | 606/181 | 2004/0204662 A1 | 10/2004 | Perez | 600/583 |
| 2004/0096991 A1 | 5/2004 | Zhang | 436/518 | 2004/0206625 A1 | 10/2004 | Bhullar | 204/403.1 |
| 2004/0098009 A1 | 5/2004 | Boecker | 606/181 | 2004/0206636 A1 | 10/2004 | Hodges | 205/792 |
| 2004/0098010 A1 | 5/2004 | Davison | 606/181 | 2004/0206658 A1 | 10/2004 | Hammerstedt | 206/524.1 |
| 2004/0102803 A1 | 5/2004 | Boecker | 606/183 | 2004/0209307 A1 | 10/2004 | Valkirs | 435/7.1 |
| 2004/0106855 A1 | 6/2004 | Brown | 600/301 | 2004/0209350 A1 | 10/2004 | Sakata | 435/287.1 |
| 2004/0106858 A1 | 6/2004 | Say | 600/345 | 2004/0209354 A1 | 10/2004 | Mathies | 435/287.2 |
| 2004/0106859 A1 | 6/2004 | Say | 600/345 | 2004/0210279 A1 | 10/2004 | Gruzdev | 607/89 |
| 2004/0106860 A1 | 6/2004 | Say | 600/345 | 2004/0211666 A1 | 10/2004 | Pamidi | 204/403.01 |
| 2004/0106904 A1 | 6/2004 | Gonnelli | 604/173 | 2004/0214253 A1 | 10/2004 | Paek | 435/7.92 |
| 2004/0106941 A1 | 6/2004 | Roe | 606/181 | 2004/0215224 A1 | 10/2004 | Sakata | 606/181 |
| 2004/0107116 A1 | 6/2004 | Brown | 705/2 | 2004/0215225 A1 | 10/2004 | Nakayama | 606/182 |
| 2004/0115754 A1 | 6/2004 | Chang | 435/14 | 2004/0216516 A1 | 11/2004 | Sato | 73/64.56 |
| 2004/0115831 A1 | 6/2004 | Meathrel | 436/514 | 2004/0217019 A1 | 11/2004 | Cai | 205/792 |
| 2004/0116780 A1 | 6/2004 | Brown | 600/300 | 2004/0219500 A1 | 11/2004 | Brown | 434/307 R |
| 2004/0116829 A1 | 6/2004 | Raney | 600/573 | 2004/0219535 A1 | 11/2004 | Bell | 435/6 |
| 2004/0117207 A1 | 6/2004 | Brown | 705/2 | 2004/0220456 A1 | 11/2004 | Eppstein | 600/309 |
| 2004/0117208 A1 | 6/2004 | Brown | 705/2 | 2004/0220495 A1 | 11/2004 | Cahir | 600/562 |
| 2004/0117209 A1 | 6/2004 | Brown | 705/2 | 2004/0220564 A1 | 11/2004 | Ho | 606/47 |
| 2004/0117210 A1 | 6/2004 | Brown | 705/2 | 2004/0220603 A1 | 11/2004 | Rutynowski | 606/181 |
| 2004/0122339 A1 | 6/2004 | Roe | | 2004/0222092 A1 | 11/2004 | Musho | 204/401 |
| 2004/0127818 A1 | 7/2004 | Roe | 600/583 | 2004/0224369 A1 | 11/2004 | Cai | 435/7.7 |
| 2004/0127819 A1 | 7/2004 | Roe | 600/583 | 2004/0225230 A1 | 11/2004 | Liamos | 600/583 |

| Publication No. | Date | Name | Class |
|---|---|---|---|
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Imants Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/22 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Katsuji | 422/58 |
| 2005/0036909 A1 | 2/2005 | Erickson | 422/61 |
| 2005/0037482 A1 | 2/2005 | Erikson | 422/61 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0059895 A1 | 3/2005 | Brown | 600/481 |
| 2005/0060194 A1 | 3/2005 | Brown | 705/2 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |

| Publication No. | Date | Name | Class |
|---|---|---|---|
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245795 A1 | 11/2005 | Yamaguchi | 600/345 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Day | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004271 A1 | 1/2006 | Bedard | 600/316 |
| 2006/0004272 A1 | 1/2006 | Peyser | 600/362 |
| 2006/0004582 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030788 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |

| Pub. No. | Date | Name | Class |
|---|---|---|---|
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1* | 8/2006 | Freeman et al. | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231442 A1 | 10/2006 | Windus-Smith | 206/438 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |

| | | | | | | |
|---|---|---|---|---|---|---|
| 2007/0016103 | A1 | 1/2007 | Calasso ............... 600/583 | GB | 2335990 A | 10/1999 |
| 2007/0016104 | A1 | 1/2007 | Jansen ............... 600/583 | WO | WO 80/01389 | 7/1980 |

FOREIGN PATENT DOCUMENTS

| | | |
|---|---|---|
| DE | 29824204 | 10/2000 |
| DE | 10032042 | 1/2002 |
| DE | 10057832 | 2/2002 |
| DE | 10057832 C1 | 2/2002 |
| DE | 10142232 | 3/2003 |
| DE | 10208575 C1 | 8/2003 |
| DE | 10245721 | 12/2003 |
| DE | 10361560 A1 | 7/2005 |
| EP | 0199484 A2 | 10/1986 |
| EP | 0289 269 | 11/1988 |
| EP | 0320109 | 6/1989 |
| EP | 0170375 | 5/1990 |
| EP | 0136362 | 12/1990 |
| EP | 0453283 | 10/1991 |
| EP | 0263948 | 2/1992 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0560336 | 5/1998 |
| EP | 0878 708 | 11/1998 |
| EP | 0505475 | 3/1999 |
| EP | 0901018 | 3/1999 |
| EP | 0470649 | 6/1999 |
| EP | 0847447 | 11/1999 |
| EP | 0964059 | 12/1999 |
| EP | 0969097 | 1/2000 |
| EP | 1021950 | 7/2000 |
| EP | 0894869 | 2/2001 |
| EP | 1074832 | 2/2001 |
| EP | 1093854 | 4/2001 |
| EP | 1101443 | 5/2001 |
| EP | 1114995 | 7/2001 |
| EP | 0736607 | 8/2001 |
| EP | 0874984 | 11/2001 |
| EP | 0730037 | 12/2001 |
| EP | 0636879 | 1/2002 |
| EP | 01174083 | 1/2002 |
| EP | 0851224 | 3/2002 |
| EP | 0759553 | 5/2002 |
| EP | 0856586 | 5/2002 |
| EP | 0817809 | 7/2002 |
| EP | 0872728 | 7/2002 |
| EP | 0795748 | 8/2002 |
| EP | 0685737 | 9/2002 |
| EP | 0958495 | 11/2002 |
| EP | 0937249 | 12/2002 |
| EP | 0880692 | 1/2004 |
| EP | 01374770 | 1/2004 |
| EP | 1246688 | 5/2004 |
| EP | 1502614 | 2/2005 |
| GB | 2168815 | 6/1986 |
| GB | 233936 A | 6/1999 |
| GB | 2335860 A | 10/1999 |
| WO | WO 85/04089 | 9/1985 |
| WO | WO 86/07632 | 12/1985 |
| WO | WO 91/09139 | 6/1991 |
| WO | WO 93/06979 | 4/1993 |
| WO | WO 93/25898 | 12/1993 |
| WO | WO 94/27140 | 11/1994 |
| WO | WO 94/29703 | 12/1994 |
| WO | WO 94/29704 | 12/1994 |
| WO | WO 94/29731 | 12/1994 |
| WO | WO 95/00662 | 1/1995 |
| WO | WO 95/10223 | 4/1995 |
| WO | WO 95/22597 | 8/1995 |
| WO | WO 96/30431 | 10/1996 |
| WO | WO 97/02359 | 1/1997 |
| WO | WO 97/02487 | 1/1997 |
| WO | WO 97/18464 | 5/1997 |
| WO | WO 97/30344 | 8/1997 |
| WO | WO 97/42882 | 11/1997 |
| WO | WO 97/45720 | 12/1997 |
| WO | WO 98/03431 | 1/1998 |
| WO | WO 98/19159 | 5/1998 |
| WO | WO 98/20332 | 5/1998 |
| WO | WO 98/20348 | 5/1998 |
| WO | WO 98/24366 | 6/1998 |
| WO | WO 98/24373 | 6/1998 |
| WO | WO 98/35225 | 8/1998 |
| WO | WO 99/03584 | 1/1999 |
| WO | WO 99/05966 | 2/1999 |
| WO | WO 99/07431 A1 | 2/1999 |
| WO | WO 99/13100 | 3/1999 |
| WO | WO 99/17854 | 4/1999 |
| WO | WO 99/18532 | 4/1999 |
| WO | WO 99/19507 | 4/1999 |
| WO | WO 99/19717 | 4/1999 |
| WO | WO 99/27483 | 6/1999 |
| WO | WO 99/27852 | 6/1999 |
| WO | WO 99/62576 | 12/1999 |
| WO | WO 99/64580 | 12/1999 |
| WO | WO 00/06024 | 2/2000 |
| WO | WO 00/09184 | 2/2000 |
| WO | WO 00/11578 | 3/2000 |
| WO | WO 00/15103 | 3/2000 |
| WO | WO 00/17799 | 3/2000 |
| WO | WO 00/17800 | 3/2000 |
| WO | WO 00/18293 | 4/2000 |
| WO | WO 00/19346 | 4/2000 |
| WO | WO 00/30186 | 5/2000 |
| WO | WO 00/32097 | 6/2000 |
| WO | WO 00/32098 | 6/2000 |
| WO | WO 00/33236 | 6/2000 |
| WO | WO 00/42422 | 6/2000 |
| WO | WO 00/39914 | 7/2000 |
| WO | WO 00/44084 | 7/2000 |
| WO | WO 00/50771 | 8/2000 |
| WO | WO 00/60340 | 10/2000 |
| WO | WO 00/64022 | 10/2000 |
| WO | WO 00/67245 | 11/2000 |
| WO | WO 00/67268 | 11/2000 |
| WO | WO 00/72452 | 11/2000 |
| WO | WO 01/00090 | 1/2001 |
| WO | WO 01/75433 | 3/2001 |
| WO | WO 01/23885 | 4/2001 |
| WO | WO 01/25775 | 4/2001 |
| WO | WO 01/26813 | 4/2001 |
| WO | WO 01/33216 | 5/2001 |
| WO | WO 01/34029 | 5/2001 |
| WO | WO 01/36955 | 5/2001 |
| WO | WO 01/37174 | 5/2001 |
| WO | WO 01/40788 | 7/2001 |
| WO | WO 01/57510 | 9/2001 |
| WO | WO 01/64105 | 9/2001 |

| | | |
|---|---|---|
| WO | WO 01/69505 | 9/2001 |
| WO | WO 01/72225 | 10/2001 |
| WO | WO 01/73124 | 10/2001 |
| WO | WO 01/73395 | 10/2001 |
| WO | WO 01/89691 | 11/2001 |
| WO | WO 02/00101 | 1/2002 |
| WO | WO 02/02796 | 1/2002 |
| WO | WO 02/08750 | 1/2002 |
| WO | WO 02/08753 | 1/2002 |
| WO | WO 02/008950 | 1/2002 |
| WO | WO 02/18940 | 3/2002 |
| WO | WO 02/21317 | 3/2002 |
| WO | WO 02/25551 | 3/2002 |
| WO | WO 02/32559 | 4/2002 |
| WO | WO 02/41227 | 5/2002 |
| WO | WO 02/41779 | 5/2002 |
| WO | WO 02/44948 | 6/2002 |
| WO | WO 02/059734 | 8/2002 |
| WO | WO 02/069791 | 9/2002 |
| WO | WO 02/077638 | 10/2002 |
| WO | WO 02/100251 | 12/2002 |
| WO | WO 02/100252 | 12/2002 |
| WO | WO 02/100253 | 12/2002 |
| WO | WO 02/100254 | 12/2002 |
| WO | WO 02/100460 | 12/2002 |
| WO | WO 02/100461 | 12/2002 |
| WO | WO 02/101343 | 12/2002 |
| WO | WO 02/101359 | 12/2002 |
| WO | WO 03/000321 | 1/2003 |
| WO | WO 03/023389 | 3/2003 |
| WO | WO 03/042691 | 5/2003 |
| WO | WO 03/045557 | 6/2003 |
| WO | WO 03/046542 | 6/2003 |
| WO | WO 03/049609 | 6/2003 |
| WO | WO 03/050534 | 6/2003 |
| WO | WO 03/066128 | 8/2003 |
| WO | WO 03/070099 | 8/2003 |
| WO | WO 03/071940 | 9/2003 |
| WO | WO 03/088851 A1 | 10/2003 |
| WO | WO 03/094752 | 11/2003 |
| WO | WO 03/101297 | 12/2003 |
| WO | WO 2004/008130 | 1/2004 |
| WO | WO 2004/022133 | 3/2004 |
| WO | WO 2004/026130 | 4/2004 |
| WO | WO 2004/040285 A2 | 5/2004 |
| WO | WO 2004/040287 A1 | 5/2004 |
| WO | WO 2004/040948 | 5/2004 |
| WO | WO 2004/041082 | 5/2004 |
| WO | WO 2004/054455 | 7/2004 |
| WO | WO 2004/060174 | 7/2004 |
| WO | WO 2004/060446 | 7/2004 |
| WO | WO 2004/091693 | 10/2004 |
| WO | WO 2004/098405 | 11/2004 |
| WO | WO 2004/003147 | 12/2004 |
| WO | WO 2004/107964 | 12/2004 |
| WO | WO 2004/107975 | 12/2004 |
| WO | WO 2004/112602 | 12/2004 |
| WO | WO 2005/001418 | 1/2005 |
| WO | WO 2005/006939 | 1/2005 |
| WO | WO 2005/011774 | 2/2005 |
| WO | WO 2005/016125 | 2/2005 |
| WO | WO 2005/018425 | 3/2005 |
| WO | WO 2005/018430 | 3/2005 |
| WO | WO 2005/018454 | 3/2005 |
| WO | WO 2005/018709 | 3/2005 |
| WO | WO 2005/018710 | 3/2005 |
| WO | WO 2005/018711 | 3/2005 |
| WO | WO 2005/022143 | 3/2005 |
| WO | WO 2005/023088 | 3/2005 |
| WO | WO 2005/033659 | 4/2005 |
| WO | WO 2005/034720 | 4/2005 |
| WO | WO 2005/034721 | 4/2005 |
| WO | WO 2005/034741 | 4/2005 |
| WO | WO 2005/034778 | 4/2005 |
| WO | WO 2005/035017 | 4/2005 |
| WO | WO 2005/035018 | 4/2005 |
| WO | WO 2005/037095 | 4/2005 |
| WO | WO 2005/046477 | 5/2005 |
| WO | WO 2005/065399 | 7/2005 |
| WO | WO 2005/065414 | 7/2005 |
| WO | WO 2005/065415 | 7/2005 |
| WO | WO 20065545 A2 | 7/2005 |
| WO | WO 2005/072604 | 8/2005 |
| WO | WO 2005/084557 | 9/2005 |
| WO | WO 2005/116622 | 12/2005 |
| WO | WO 2005/119234 | 12/2005 |
| WO | WO 2005/121759 | 12/2005 |
| WO | WO 2006/001973 | 1/2006 |
| WO | WO 2006/011062 | 2/2006 |
| WO | WO 2006/013045 | 2/2006 |
| WO | WO 2006/027702 A2 | 3/2006 |
| WO | WO 2006/032391 | 3/2006 |
| WO | WO 2006/072004 | 7/2006 |

OTHER PUBLICATIONS

International Search Report (PCT/ISA/220) for PCT/US02/19054. (all references are being submitted herewith or were submitted in a previous Information Disclosure Statement).
International Search Report (PCT/ISA/220) for PCT/US02/19059. (all references are being submitted herewith or were submitted in a previous Information Disclosure Statement).
Written Opinion (certain documents cited) for PCT/US02/19059. (all references are being submitted herewith or were submitted in a previous Information Disclosure Statement).
International Search Report (PCT/ISA/220) for PCT/US02/19060. (all references are being submitted herewith or were submitted in a previous Information Disclosure Statement).
International Search Report (PCT/ISA/220) for PCT/US02/19450. (all references are being submitted herewith or were submitted in a previous Information Disclosure Statement).
International Search Report (PCT/ISA/220) for PCT/US02/19057. (all references are being submitted herewith or were submitted in a previous Information Disclosure Statement).
International Search Report (PCT/ISA/220) for PCT/US02/19053. (all references are being submitted herewith or were submitted in a previous Information Disclosure Statement).
International Search Report (PCT/ISA/220) for PCT/US02/19188. (all references are being submitted herewith or were submitted in a previous Information Disclosure Statement).
International Search Report (PCT/ISA/220) for PCT/US02/12555. (all references are being submitted herewith or were submitted in a previous Information Disclosure Statement).
International Search Report (PCT/ISA/220) for PCT/US02/12381. (all references are being submitted herewith or were submitted in a previous Information Disclosure Statement).
International Search Report (PCT/ISA/220) for PCT/US02/12546. (all references are being submitted herewith or were submitted in a previous Information Disclosure Statement).
International Search Report (PCT/ISA/220) for PCT/US03/35015. (all references are being submitted herewith or were submitted in a previous Information Disclosure Statement).
International Search Report (PCT/ISA/220) for PCT/US02/40095. (all references are being submitted herewith or were submitted in a previous Information Disclosure Statement).
International Search Report (PCT/ISA/220) for PCT/US02/41747. (all references are being submitted herewith or were submitted in a previous Information Disclosure Statement).

* cited by examiner

INTEGRATED BLOOD SAMPLING ANALYSIS SYSTEM WITH MULTI-USE SAMPLING MODULE

TECHNICAL FIELD

Biochemical analysis of blood samples is an important diagnostic tool for determination of patient status. Analysis of a blood sample for glucose level can provide a powerful tool for diabetics who require tight control of blood glucose levels in an effort to minimize the deleterious long-term effects of the disease. At this time, noninvasive blood analysis technology does not provide the accuracy and specificity required for clinical testing, so that test samples are mainly derived from blood, interstitial fluid, urine or saliva. Many point of care tests are performed directly on capillary whole blood, which is typically obtained by making a small incision on a finger using a hand-held lancing device. The hand-held lancing device usually includes a lancet that is rapidly displaced to penetrate the finger, creating a small wound from which a blood droplet forms on the surface of the skin after the lancet has retracted from the incision.

In addition to the lancet, patients typically deal with numerous other individual components each time a blood test is conducted, e.g. a separate lancet driver, individual testing strips, and a test strip reader. Each time blood testing is performed, the user must prepare the individual components, unwrapping and/or joining them, performing a series of steps to obtain a sample of blood from the lanced skin. Generally, the blood droplet must be placed on a sample assay strip in the proper manner, and the sample assay strip is analyzed using a measurement apparatus, or reader. After each test, the components must then be separated and the disposables (i.e. lancets and test strips) discarded properly.

BACKGROUND ART

The process of acquiring and testing a blood sample using these conventional devices can be painful and often involves numerous steps, the outcome of which is to reduce patient compliance with the frequent self testing regimens required for disease management. In addition to the pain and the paraphernalia required for self-testing, the success rate of obtaining an adequate blood sample is not 100%. The success rate can be affected by the reproducibility of the lancing technique used (due to variation in skin hydration and thickness, calluses, etc.) as well as the ability to obtain the blood droplet from the incision. Current industry standard lancet and lancing devices can have as low as a 50% success rate in generating a blood sample from the fingertip. The diabetic wishing to adhere to the optimal 5-6 times a day self testing regimen would, in essence, need to lance themselves an average of 10-12 times just to obtain the blood samples required. The more successful lancing devices are, in reality, about 80-90% successful.

What is needed is an improved method for sampling and analyzing bodily fluid which is convenient and cost efficient resulting in a simplified procedure for extraction and analysis of blood samples at the patient's side.

DISCLOSURE OF INVENTION

Embodiments of the invention relate generally to analysis of bodily fluids. The invention more specifically relates to a disposable sampling module capable of being used multiple times before being discarded.

Embodiments of the invention, including a system for collecting capillary blood are described which incorporates a disposable sampling module. Simplified actuation, lancing, sample acquisition, testing, and readout, are provided all in a handheld apparatus. A sampling module embodiment contains many individual sampling segments, each of which allows the collection and testing of a sample of blood. This allows the sampling module to be used numerous times before exchange with a new module and disposal of the used module becomes necessary, thus reducing the need to dispose of used materials after each test. The sampling module embodiment also retains used sampling materials safely, thereby reducing the problem of handling biohazardous materials.

Previously, it was necessary for the user of a lancet to go through a series of steps to obtain and analyze a blood sample, including preparing components (e.g. lancets, test strips, etc.) cocking a lancet driver, triggering the driver to fire the lancet, manually depositing a blood sample into a sample storage or analysis area, and safe disposal of used testing materials upon completion of the test. The system of embodiments of the current invention makes the blood collection process more convenient to the user by eliminating the need for the user to repeatedly perform many of these steps.

A sampling module embodiment provides for a simplified blood sampling and analysis process by having fewer components requiring assembly by the user and reducing the frequency that the components must be assembled for testing. A single sampling segment combines the lancet and testing means; reducing the task of assembly by the user. The sampling module combines many such sampling segments in unit package that fits cassette-like into a reader device. This multiuse sampling module need only be removed and replaced after all of the sampling segments are used, further reducing the task of assembly (and disassembly and disposal) by the user. In one possible configuration, a lancet driver is provided by a separate apparatus. In other embodiments the lancet driver is included in the reader device or is integrated directly on the sampling module.

Techniques for extracting a sample of human blood for the measurement of one or more of its constituents are described, such as might be used for routine monitoring of a chronic condition such as diabetes mellitus. The techniques simplify the extraction and transfer of the blood sample, and reduce the inconvenience of the process. The techniques can be advantageously used in, for example, blood glucose monitoring, coagulation testing, point-of-care stat testing to monitor patient condition over time. The techniques may be used in the clinical setting or for home use or other field settings, such as battlefield, airline, or cruise ship use.

One embodiment includes a miniaturized system which may be easily carried by the user, e.g. in a small purse or a jacket pocket. Since sampling is frequently unsuccessful due to obtaining inadequate sample volume, a miniature system to reliably obtain and analyze small, samples would improve user acceptance of the sampling procedure.

In another embodiment, a method of providing more convenient blood sampling is also described, wherein steps associated with preparation of lancing and testing materials are eliminated or rendered less frequent. In the method, a series of blood samples may be collected and tested using a single disposable sampling module which is designed to couple to a reader device. The sampling module has a plurality of sampling segments, each sampling segment adapted to be used for a single blood sampling cycle. The method starts with coupling of the sampling module and reader device and then initiating a blood sampling cycle. Upon completion of the blood sampling cycle, the sampling module is advanced to bring a fresh, unused sampling segment online, ready to perform another blood sampling cycle. After a series of blood sampling cycles has been performed and all (or substantially all) of the sampling segments have been used, the sampling module is decoupled from the reader device and discarded, leaving the reader device ready to be coupled with a new sampling module.

BRIEF DESCRIPTION OF DRAWING

The objects, advantages and features of this invention will be more readily appreciated from the following detailed description, when read in conjunction with the accompanying drawing, in which.

BEST MODE FOR CARRYING OUT THE INVENTION

Figure 1:
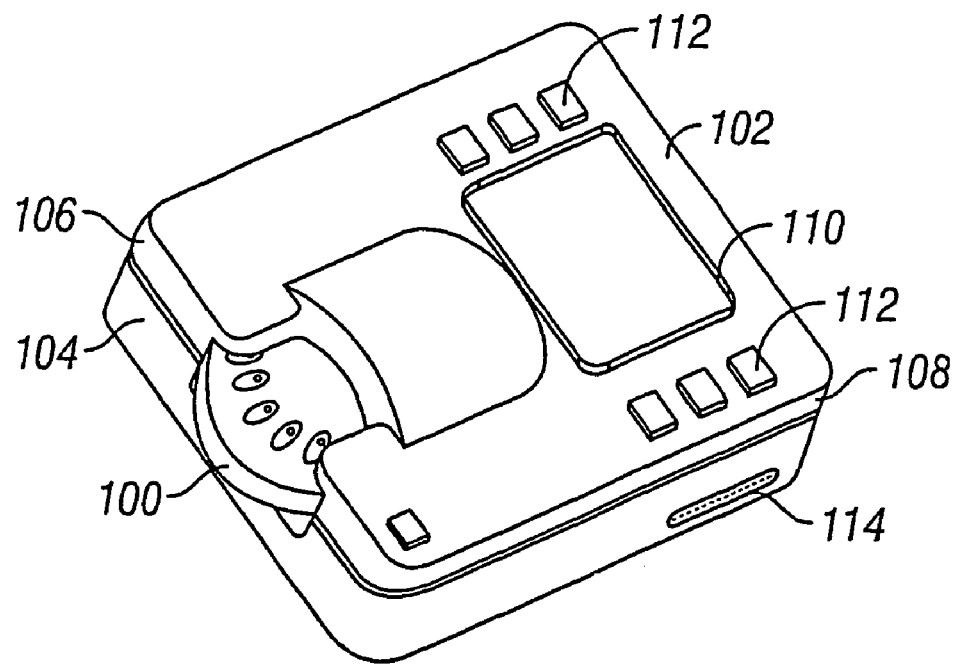
FIG. 1 illustrates a blood sampling system having features of the current invention.

U.S. Pat. Nos. 3,030,059, 3,626,929, 4,360,016, 4,608, 997, 4,622,974, 4,627,445, 4,637,403, 4,648,408, 4,653,513, 4,873,993, 4,883,068, 4,895,147, 4,920,977, WO 97/42882, U.S. Pat. Nos. 5,047,044, 5,871,494, 5,971,941, 6,071,294, 6,036,924, 5,714,390, 5,801,057, 5,632,410, 5,510,266, 5,500,071, 5,571,410 and 5,645,702 are hereby incorporated by reference in their entirety.

It is to be understood that both the foregoing general description and the following detailed description are exemplary and explanatory only and are not restrictive of the invention, as claimed. It must be noted that, as used in the specification and the appended claims, the singular forms "a", "an" and "the" include plural referents unless the context clearly dictates otherwise. Thus, for example, reference to "a material" includes mixtures of materials, reference to "a chamber" includes multiple chambers, and the like.

In this specification and in the claims which follow, reference will be made to a number of terms which shall be defined to have the following meanings:

"Integrated" as used herein means that two or more functions are conducted without intervention by the user: the "integrated" blood sampling system contains the mechanisms for a plurality. of functions, e.g., lancing, blood sample collection and testing, conveying information about the sample to the reader device, and advancing the sampling module to bring the next sampling segment online. The group of functions is carried out as the result a single initiating act by the user (i.e. each function does not have to be separately initiated by the user). In the context of a combined reader device/sampling module, integrated means that actuation of the lancet driver, lancing of the skin, sample collection and analysis, display of the test results, and (optionally) advancement of the sampling module to the next position all may occur as the result of a single simple motion by the user, such as pressing the apparatus against the skin to be sampled or touching a button to trigger the lancet driver. In another embodiment, the step of providing a calibration measurement is integrated with the previously mentioned steps. If a device is "configured to allow integrated steps A, B, and C", then steps A, B, and C all follow as a result of a single initiating action. "Unit" when used in relation to the sampling module, or portions of the sampling module, means that the components in the sampling module are assembled into a single housing, so that multiple sampling segments are contained on a single 'unit' device.

"Optional" or "optionally" means that the subsequently described circumstance may or may not occur, so that the description includes instances where the circumstance occurs and instances where it does not. For example, if a device optionally contains a feature for analyzing a blood sample, this means that the analysis, feature may or may not be present, and, thus, the description includes structures wherein a device possesses the analysis feature and structures wherein the analysis feature is not present.

"Testing means" refers to any use, singly or in combination, of chemical test reagents and methods, electrical test circuits and methods, physical test components and methods, optical test components and methods, and biological test reagents and methods to yield information about a blood sample. Such methods are well known in the art and may be based on teachings of, e.g. Tietz Textbook of Clinical Chemistry, 3d Ed., Sec. V, pp. 776-78 (Burtis & Ashwood, Eds., W.B. Saunders Company, Philadelphia, 1999); U.S. Pat. No. 5,997,817 to Chrismore et al. (Dec. 7, 1999); U.S. Pat. No. 5,059,394 to Phillips et al. (Oct. 22, 1991); U.S. Pat. No. 5,001,054 to Wagner et al. (Mar. 19, 1991); and U.S. Pat. No. 4,392,933 to Nakamura et al. (Jul. 12, 1983), the teachings of which are hereby incorporated by reference, as well as others. Testing means may include sensors in the sample test chamber that test electrochemical properties of the blood, or they may include optical means for sensing optical properties of the blood (e.g. oxygen saturation level), or they may include biochemical reagents (e.g. antibodies) to sense properties (e.g. presence of antigens) of the blood. Said testing means may be present at, e.g., a "test site" or an "analytical site." The testing means may comprise biosensing or reagent material that will react with an analyte in the blood (e.g. glucose) so that an appropriate signal correlating with the presence of the analyte is generated and can be read by the reader apparatus. Testing means are "associated with" a chamber or other structure when the testing means participates in the function of providing an appropriate signal about the blood sample to the reader device. "Calibrant testing means" refers to testing means used to test a calibrant.

"Lancet" means any sharp member used to puncture the skin for the purpose of cutting blood vessels and allowing blood to flow to the surface of the skin. The lancet has certain parameters such as diameter or width to define the cross-sectional area of the member, and geometry to define the shape of the distal or front lancing end of the member. "Lancet driver" means any means for propelling the lancet to puncture the skin. Examples of lancets and lancet drivers are well known in the art and are described herein with relation to the invention.

The term "embossing" is used to refer to a process for forming polymer, metal or ceramic shapes by bringing an embossing die into contact with a pre-existing blank of polymer, metal or ceramic. A controlled force is applied between the embossing die and the pre-existing blank of material such that the pattern and shape determined by the embossing die is pressed into the pre-existing blank of polymer, metal or ceramic. The term "embossing" encompasses "hot embossing" which is used to refer to a process for forming polymer, metal or ceramic shapes by bringing an embossing die into contact with a heated pre-existing blank of polymer, metal or ceramic. The pre-existing blank of material is heated such that it conforms to the embossing die as a controlled force is applied between the embossing die and the pre-existing blank. The resulting polymer, metal or ceramic shape is cooled and then removed from the embossing die.

The term "injection molding" is used to refer to a process for molding plastic or nonplastic ceramic shapes by injecting a measured quantity of a molten plastic or ceramic substrate into dies (or molds). In one embodiment of the present invention, components of miniaturized devices can be produced using injection molding.

References cited herein are hereby incorporated by reference in their entirety, except to the extent that they conflict with teachings explicitly set forth in this specification.

Referring to FIG. 1, a blood sampling system incorporating a disposable sampling module 100 and a reader device 102 are shown. The reader device 102 includes a deck 104 having a lid 106 attached to the deck by hinges along the rear edge of the system 108. A readout display 110 on the lid 106 functions to give the user information about the status of the reader device 102 and/or the sampling module 100, or to give a readout of a blood test. The reader device 102 has several function buttons 112 for controlling function of the reader device 102 or for inputting information into the reader device 102. Alternatively, the reader device may have a touch-sensitive screen, an optical scanner, or other input means known in the art. A reader device with an optical scanner may be particularly useful in a clinical setting, where patient information may be recorded using scan codes on patients' wristbands or files. The reader device may have a memory, enabling the reader device to store results of many recent tests. The reader device may also have a clock and calendar function, enabling the results of tests stored in the memory to be time- and date-stamped. A computer interface 114 enables records in memory to be exported to a computer. The reader device 102 has a chamber located between the deck 104 and the lid 106 which closely accommodates a sampling module 100. The chamber is accessed by raising the lid 106, allowing a sampling module 100 to be inserted or removed.

Figure 2:
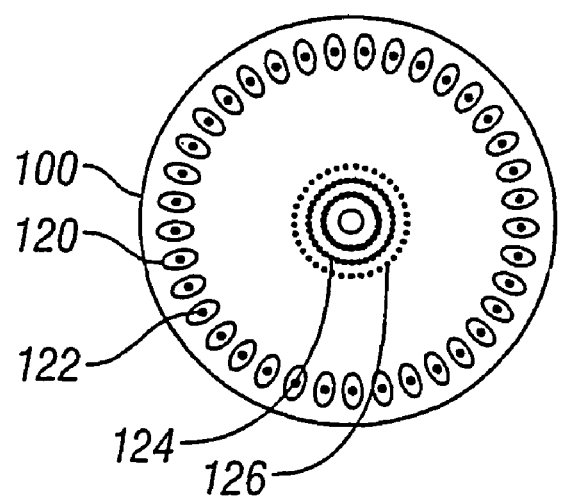
FIG. 2 is a view of the top surface of a sampling module.

FIG. 2 is an illustration showing some of the features of an embodiment of a sampling module. The sampling module 100 has a housing having an orientation sensitive contact interface for mating with a complementary surface on the reader device. The contact interface functions to align the sampling module with the reader device, and also allows the reader device to rotate the sampling module in preparation for a new sampling event. The contact interface may take the form of cogs or grooves formed in the housing which mate with complementary cogs or grooves in the chamber of the reader device. The sampling module has a plurality of sampling sites 120 on the housing, which are shown as slightly concave depressions near the perimeter of the sampling module 100. Each sampling site defines an opening 122 contiguous with a sampling port entering the sampling module. In an alternate embodiment, the sampling sites and sampling ports are located on the edge of the sampling module. Optical windows 124 allow transmission of light into the sampling module for the purpose of optically reading test results. Alternatively, sensor connection points allow transmission of test results to the reader device via electrical contact. Access ports 126, if present, allow transmission of force or pressure into the sampling module from the reader device. The access ports may be useful in conjunction with running a calibration test or combining reagents with sampled blood.

The described features are arranged around the sampling module, and the sampling module is radially partitioned into many sampling segments, each sampling segment having the components necessary to perform a single blood sampling and testing event. A plurality of sampling segments are present on a sampling module, generally at least ten sampling segments are present on a single disposable sampling module; at least about 20, or more on some embodiments, and at least about 34 sampling segments are present on one embodiment, allowing the sampling module to be maintained in the reader device for about a week before replacing with a new sampling module (assuming five sampling and testing events per day for seven days). With increasing miniaturization, up to about 100, or more preferably up to about 150, sampling segments may be included on a single sampling module, allowing up to a month between replacements with new sampling modules. It may be necessary for sampling sites to be located in several concentric rings around the sampling module (or otherwise packed onto the housing surface) to allow the higher number of sampling segments on a single sampling module. In other embodiments, the sampling module may be any other shape which may conveniently be inserted into a reader device and which are designed to contain multiple sampling segments, e.g. a square, rectangular, oval, or polygonal shape. Each sampling segment is miniaturized, being generally less than about 6.0 cm long by about 1.0 cm wide by about 1.0 cm thick, so that thirty five more or less wedge-shaped sampling segments can fit around a disk having a radius of about 6.0 cm. Preferably, each sampling segment is much smaller, e.g. less than about 3.0 cm long by about 0.5 cm wide by about 0.5 cm thick.

Figure 3:
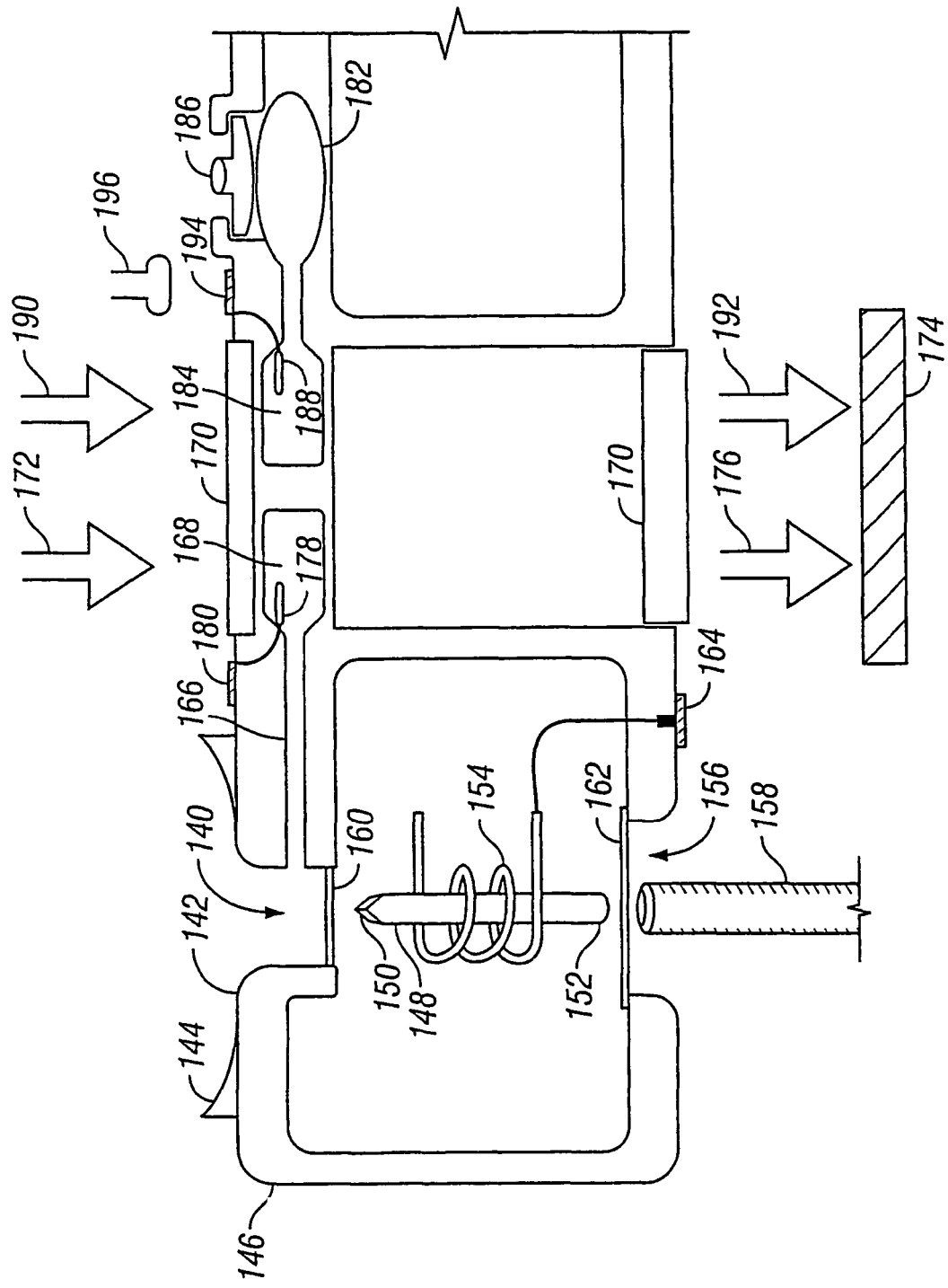
FIG. 3 schematically depicts a sampling segment of the sampling module in place in the reader device.

FIG. 3 depicts, in a highly schematic way, a single sampling segment, positioned within the reader device. Of course, it will occur to the person of ordinary skill in the art that the various recited components may be physically arranged in various configurations to yield a functional system. FIG. 3 depicts some components which might only be present in alternate embodiments and are not necessarily all present in any single embodiment. The sampling segment has a sampling port 140 which is contiguous with an opening 142 defined by a sampling site 144 on the sampling module housing 146. A lancet 148 having a lancet tip 150 adjacent to the sampling port 140 is operably maintained within the housing such that the lancet 148 can move to extend the lancet tip 150 through the sampling port 140 to outside of the sampling module. The lancet 148 also has a lancet head 152 opposite the lancet tip. The lancet 148 is driven to move by a lancet driver 154, which is schematically depicted as a coil around the lancet 148. The lancet driver 154 optionally is included in the sampling module (as pictured) or alternatively is external to the sampling module. The sampling segment, may further include a driver port 156 defined by the housing adjacent to the lancet head 152—the driver port 156 allows an external lancet driver 158 access to the lancet 148. In embodiments where the lancet driver 154 is in the sampling module, it may be necessary to have a driver connection point 164 upon the housing accessible to the reader device. The driver connection point 164 may be a means of triggering the lancet driver 154 or of supplying motive force to the lancet driver 154, e.g. an electrical current to an electromechanical lancet driver. In one embodiment a pierceable membrane 160 is present between the lancet tip 150 and the sampling port 140, sealing the lancet 148 from any outside contact prior to use. A second membrane 162 may be present adjacent to the lancet head 152 sealing the driver port 156. The pierceable membrane 160 and the second membrane 162 function to isolate the lancet 148 within the lancet chamber to maintain sterility of the lancet 148 prior to use. During use the pierceable membrane 160 and the second membrane 162, if present, are pierced by the lancet tip 150 and the external lancet driver 158, respectively.

A capillary channel 166 leads from the sampling port 140 to a sample test chamber 168. The sample test chamber 168 is associated with a testing means capable of being read by the reader device. If the testing means is optical in nature, the testing means may include optically transparent windows 170 in the housing above and below the sample test chamber 168, allowing a light source in the reader device to pass light 172 through the sample test chamber. An optical sensor 174, e.g. a CMOS array, is present in the reader device for sensing the light 176 that has passed through the sample test chamber 168 and generating a signal to be analyzed by the reader device. In a separate embodiment, only one optically transparent window is present, and the opposing side of the sample test chamber is silvered or otherwise reflectively coated to reflect light back through the sample test chamber and out the window to be analyzed by the reader device. In an alternate embodiment, the testing means is electrochemical 178, e.g. an enzyme electrode, and includes a means of transmitting an electric current from the sampling module to the reader device, e.g. an electrical contact 180 on the housing accessible to the reader device.

In one embodiment, the pierceable membrane 160 may be made of polymer-based film that has been coated with a silicone-based gel. For example, the membrane structure may comprise a polymer-based film composed of polyethylene terephthalate, such as the film sold under the trademark MYLAR. The membrane structure may further comprise a thin coating of a silicone-based gel such as the gel sold under the trademark SYLGARD on at least one surface of the film. The, usefulness of such a film is its ability to reseal after the lancet tip has penetrated it without physically affecting the lancet's cutting tip and edges. The MYLAR film provides structural stability while the thin SYLGARD silicone laminate is flexible enough to retain its form and close over the hole made in the MYLAR film. Other similar materials fulfilling the structural stability and flexibility roles may be used in the manufacture of the pierceable membrane in this embodiment.

The pierceable membrane 160 operates to allow the lancet tip 150 to pierce the pierceable membrane 160 as the lancet tip 150 travels into and through the sampling port 140. In the described embodiment, the silicone-based gel of the membrane 160 automatically seals the cut caused by the lancet tip 150. Therefore, after an incision is made on a finger of a user and the lancet tip 150 is retracted back through the pierceable membrane 160, the blood from the incision is prevented from flowing through the pierceable membrane 160, which aids the blood to travel through the capillary channel 166 to accumulate within the sample test chamber 168. Thus the pierceable membrane 160 prevents blood from flowing into the lancet device assembly, and blood contamination and loss into the lancet device mechanism cavity are prevented. In yet another embodiment, used sampling ports are automatically sealed off before going to the next sample acquisition cycle by a simple button mechanism. A similar mechanism seals off a sampling port should sampling be unsuccessful.

In an alternate embodiment, a calibrant supply reservoir 182 is also present in each sampling segment. The calibrant supply reservoir 182 is filled with a calibrant solution and is in fluid communication with a calibration chamber 184. The calibration chamber 184 provides a source of a known signal from the sampling module to be used to validate and quantitate the test conducted in the sample test chamber 168. As such, the configuration of the calibration chamber 184 closely resembles the sample test chamber 168. During use, the calibrant solution is forced from the calibrant supply reservoir 182 into the calibration chamber 184. The figure depicts a stylized plunger 186 above the calibrant supply reservoir 182 ready to squeeze the calibrant supply reservoir 182. In practice, a variety of methods of transporting small quantities of fluid are known in the art and can be implemented on the sampling module. The calibration chamber 184 is associated with a calibrant testing means. FIG. 3 shows two alternate calibrant testing means—optical windows 170 and an electrochemical sensor 188. In cases where the sampling module is designed to perform several different tests on the blood, both optical and electrochemical testing means may be present. The optical windows 170 allow passage of light 190 from the reader device through the calibration chamber 184, whereupon the light 192 leaving the calibration chamber 184 passes onto an optical sensor 174 to result in a signal in the reader device. The electrochemical sensor 188 is capable of generating a signal that is communicated to the reader device via, e.g. an electrical contact 194, which is accessible to a contact probe 196 on the reader device that can be extended to contact the electrical contact 194. The calibrant solution may be any solution which, in combination with the calibrant testing means, will provide a suitable signal which will serve as calibration measurement to the reader device. Suitable calibrant solutions are known in the art, e.g. glucose solutions of known concentration. The calibration measurement is used to adjust the results obtained from testing means from the sample test chamber.

To maintain small size in some sampling module embodiments, allowing small quantities of sampled blood to be sufficient, each component of the sampling segment must be small, particularly the capillary channel and the sample test chamber. The capillary channel can be less than about 0.5 mm in diameter, specifically less than about 0.3 mm in diameter, more specifically less than about 0.2 mm in diameter, and even more specifically less than about 0.1 mm in diameter. The capillary channel may generally be at least about 50 micrometers in diameter. The dimensions of the sample test chamber may be less than about 1 mm by about 1 mm by about 1 mm, specifically less than about 0.6 mm by about 0.6 mm by about 0.4 mm, more specifically less than about 0.4 mm by 0.4 mm by 0.2 mm, and even more specifically less than about 0.2 mm by about 0.2 mm by about 0.1 mm. The sampling test chamber can generally be at least about 100 micrometers by 100 micrometers by 50 micrometers. The sampling module is able to return a valid testing result with less than about 5 microliters of blood taken from the skin of a patient, specifically less than about 1 microliter, more specifically less than about 0.4 microliters, and even more specifically less than about. 0.2 microliters. Generally, at least 0.05 microliters of blood is drawn. for a sample.

The sample module housing may be made in a plurality of distinct pieces which are then assembled to provide the completed housing. The distinct pieces may be manufactured from a wide range of substrate materials. Suitable materials for forming the described apparatus include, but are not limited to, polymeric materials, ceramics (including aluminum oxide and the like), glass, metals, composites, and laminates thereof. Polymeric materials are particularly preferred herein and will typically be organic polymers that are either homopolymers or copolymers, naturally occurring or synthetic, crosslinked or uncrosslinked. It is contemplated herein to form portions of the sampling modules of substrates including materials such as the following: polycarbonates; polyesters, including poly(ethylene terephthalate) and poly (butylene terephthalate); polyamides, (such as nylons); polyethers, including polyformaldehyde and poly(phenylene sulfide); polyimides, such as that manufactured under the trademarks KAPTON (DuPont, Wilmington, Del.) and UPILEX (Ube Industries, Ltd., Japan); polyolefin compounds, including ABS polymers, Kel-F copolymers, poly (methyl methacrylate), poly(styrene-butadiene) copolymers, poly(tetrafluoroethylene), poly(ethylenevinyl acetate) copolymers, poly(N-vinylcarbazole) and polystyrene.

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One composite material is a polyimide laminate formed from a first layer of polyimide such as KAPTON polyimide, available from DuPont (Wilmington, Del.), that has been co-extruded with a second, thin layer of a thermal adhesive form of polyimide known as KJ®, also available from DuPont (Wilmington, Del.).

The invention in its various embodiments can be fabricated using any convenient method, including, but not limited to, molding and casting techniques, embossing methods, surface machining techniques, bulk machining techniques, and stamping methods. Further, injection molding techniques well known in the art may be useful in shaping the materials used to produce sample modules according to the instant invention.

For some embodiments, the first time a new sampling module 100 is used, the user removes any outer packaging material from the sampling module 100 and opens the lid 106 of the reader device 102, exposing the chamber. The sampling module 100 is slipped into the chamber and the lid 106 closed. The patient's skin is positioned upon the sampling site 120 and the integrated process of lancing the skin, collecting the blood sample, and testing the blood sample is initiated, e.g. by pressing a function button 112 to cause the lancet driver to be triggered. The patient's skin is maintained in position upon the sampling site 120, adjacent the sampling port 140, until an adequate volume of blood has been collected, whereupon the system may emit a signal (e.g. an audible beep) that the patient's skin may be lifted from the sampling site 120. When the testing of the sample is complete, the reader device 102 automatically reads the results from the sampling module 100 and reports the results on the readout display 110. The reader device 102 may also store the result in memory for later downloading to a computer system. The sampling module 100 may then automatically be advanced to bring the next sampling segment inline for the next use. Each successive time the system is used (until the sampling module 100 is used up), the patient's skin may be placed upon the sampling site 120 of the (already installed) sampling module 100, thus simplifying the process of blood sampling and testing.

A method of providing more convenient blood sampling, wherein a series of blood samples may be collected and tested using a single disposable sampling module which is designed to couple to a reader device is described. Embodiments of the sampling module include a plurality of sampling segments. Each sampling segment can be adapted to perform a single blood sampling cycle and is functionally arranged within the sampling module to allow a new sampling segment to be brought online after a blood sampling cycle is completed. Each blood sampling cycle may include lancing of a patient's skin, collection of a blood sample, and testing of the blood sample. The blood sampling cycle may also include reading of information about the blood sample by the reader device, display and/or storage of test results by the reader device, and/or automatically advancing the sampling module to bring a new sampling segment online and ready for the next blood sampling cycle to begin. A method embodiment starts with coupling of the sampling module and reader device and then initiating a blood sampling cycle. Upon completion of the blood sampling cycle, the sampling module is advanced to bring a fresh, unused sampling segment online, ready to perform another blood sampling cycle. Generally, at least ten sampling segments are present, allowing the sampling module to be advanced nine times after the initial blood sampling cycle. In some embodiments, more sampling segments are present and the sampling module may be advanced about 19 times, and about 34 times in some embodiments, allowing about 19 or about 34 blood sampling cycles, respectively, after the initial blood sampling cycle. After a series of blood sampling cycles has been performed and substantially all (i.e. more than about 80%) of the sampling segments have been used, the sampling module is decoupled from the reader device and discarded, leaving the reader device ready to be coupled with a new sampling module.

Although the above-described embodiments of the present invention have been described in detail, various modifications to the present invention will become apparent to those skilled in the art from the foregoing description and accompanying drawings and will be within the scope of the invention, which is to be limited only by the following claims.

The invention claimed is:

1. An apparatus for collecting blood from a patient's skin, the apparatus comprising
a disc shaped sampling module radially partitioned into a plurality of sampling segments positioned near a periphery of the disc shaped sampling module, each sampling segment having components to perform a single blood sampling and testing event and including a sampling port, a lancet having a tip, the tip adjacent the sampling port, the lancet maintained within a housing and operable to extend the lancet tip through the sampling port to pierce the patient's skin positioned adjacent the sampling port, the disc shaped sampling module having a plurality of sample test chambers, each of a sample test chamber in fluid communication with a sampling port via a capillary channel with a diameter that is less than 0.1 mm, the sample test chambers associated with testing means, each of a sample test chamber being sized to hold no more than about 0.4 microliter of a blood sample;
a driver configured to be coupled to the lancet, the driver being associated with a driver port;
a first seal that seals each of a lancet tip prior to use;
a second seal adjacent to a lancet head that seals the driver port;
a contact interface that aligns the sampling module with a reader device; and
a rotation device coupled to the sampling module and configured to rotate the sampling module into position for a new sampling event.

2. The apparatus of claim 1, wherein each sampling segment further comprises a sampling site contoured for positioning the patients' skin, the sampling site defining an opening contiguous with the sampling port.

3. The apparatus of claim 1, wherein the sampling module includes at least 10 sampling segments.

4. The apparatus of claim 1, wherein each sampling segment is configured to allow integrated lancing, collection, and testing.

5. The apparatus of claim 1, wherein the sample test chamber is smaller than about 0.6 mm long by 0.6 mm wide by 0.4 mm deep.

6. The apparatus of claim 1, wherein each sampling segment further comprises a calibrant reservoir in fluid communication with a calibration chamber, the calibration chamber associated with calibrant testing means.

7. A blood sampling system comprising the apparatus of claim 1, the blood sampling system further comprising a reader device associated with the apparatus of claim 1.

8. The blood sampling system of claim 7 configured to allow integrated lancing of the skin, collection of blood, testing of the blood, display of information about the blood, and advancement of the apparatus of claim 1 to bring another sampling segment online.

9. A method of collecting and testing a series of blood samples, the method comprising
   a) obtaining a disc shaped sampling module that is radially portioned into a plurality of sampling segments with sample test chambers, and a reader device, each sampling segment adapted to perform a single blood sampling cycle of lancing, collecting, communicating in fluid form, and testing of a blood sample, the sampling module coupled to a rotation device to rotate the sampling module into position for a new sampling event, each of a sample test chamber in fluid communication with a sampling port via a capillary channel with a diameter that is less than 0.1 mm, the sample test chambers associated with testing means, each of a sample test chamber being sized to hold no more than about 0.4 microliter of a blood sample, a driver configured to be coupled to the lancet, the driver being associated with a driver port; a first seal that seals each of a lancet tip prior to use a second seal adjacent to a lancet head that seals the driver port; a contact interface that aligns the sampling module with a reader device,
   b) coupling the sampling module to the reader device,
   c) initiating the blood sampling cycle,
   d) using the rotating device to rotate the sampling module and advancing the sampling module to bring another sampling segment online,
   e) repeating steps c) and d) until substantially all sampling segments on the sampling module have been used, and coupling the sampling module and reader device.

10. The method of claim 9, wherein steps c) and d) may be repeated at least 10 times before performing step f).

11. The method of claim 9, wherein each sampling segment is configured to allow integrated lancing, collection, and testing.

* * * * *